(12) United States Patent
Canales et al.

(10) Patent No.: US 10,085,494 B2
(45) Date of Patent: *Oct. 2, 2018

(54) SWIMWEAR DESIGN AND CONSTRUCTION

(71) Applicant: Roka Sports, Inc., Austin, TX (US)

(72) Inventors: Robert Allen Canales, Austin, TX (US); Kurt Robert Spenser, Burbank, CA (US)

(73) Assignee: ROKA SPORTS, INC., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/790,637

(22) Filed: Oct. 23, 2017

(65) Prior Publication Data

US 2018/0055099 A1 Mar. 1, 2018

Related U.S. Application Data

(63) Continuation of application No. 15/484,707, filed on Apr. 11, 2017, which is a continuation of application
(Continued)

(51) Int. Cl.
*A41D 7/00* (2006.01)
*A61B 5/00* (2006.01)
(Continued)

(52) U.S. Cl.
CPC ............... *A41D 7/00* (2013.01); *A41D 1/002* (2013.01); *A41D 13/012* (2013.01);
(Continued)

(58) Field of Classification Search
CPC ........ A41D 7/00; A41D 1/002; A41D 13/012; A41D 13/00; A41D 13/0125;
(Continued)

(56) References Cited

U.S. PATENT DOCUMENTS 1,731,695 A  10/1929  Wright
2,462,361 A   2/1949  Cassens
(Continued)

FOREIGN PATENT DOCUMENTS

FR   2566320 A1   12/1985
GB   2259237 A     3/1993
(Continued)

OTHER PUBLICATIONS

2012 Bluseventy "full sleeve" Reaction wetsuit. http://www.superiormantri.com/shop. (4 pages) (Nov. 20, 2012).
(Continued)

*Primary Examiner* — Gloria Hale
(74) *Attorney, Agent, or Firm* — Wilson, Sonsini, Goodrich & Rosati

(57) ABSTRACT

A wetsuit is provided which comprises (a) a first central region comprising a first material and having a first thickness; and (b) a second lateral region comprising a second material and having a second thickness. The buoyancy per unit area of the first region is greater than the buoyancy per unit area of the second region.

30 Claims, 21 Drawing Sheets

Related U.S. Application Data

No. 15/346,654, filed on Nov. 8, 2016, now Pat. No. 9,661,881, which is a continuation of application No. 14/361,296, filed as application No. PCT/US2012/066879 on Nov. 28, 2012, now Pat. No. 9,572,378.

(60) Provisional application No. 61/563,885, filed on Nov. 28, 2011.

(51) Int. Cl.
| | |
|---|---|
| *A41D 1/00* | (2018.01) |
| *A61B 5/024* | (2006.01) |
| *A41D 13/012* | (2006.01) |
| *G08B 6/00* | (2006.01) |
| *A61B 5/0245* | (2006.01) |
| *G08B 21/04* | (2006.01) |

(52) U.S. Cl.
CPC ........ *A61B 5/0245* (2013.01); *A61B 5/02438* (2013.01); *A61B 5/486* (2013.01); *A61B 5/6804* (2013.01); *G08B 6/00* (2013.01); *A41D 2300/322* (2013.01); *A41D 2400/24* (2013.01); *A41D 2400/46* (2013.01); *A41D 2500/50* (2013.01); *A41D 2500/52* (2013.01); *A41D 2600/10* (2013.01); *G08B 21/0453* (2013.01)

(58) Field of Classification Search
CPC .......... A41D 2300/322; A41D 2400/24; A41D 2400/14; A41D 2600/10; A41D 2500/52; A41D 2600/106; A61B 5/020438; A61B 5/6804; A61B 5/486; A63C 11/10; A63C 11/04; A63C 11/043; A63C 11/046; A63C 9/11; A63C 9/093; A63C 9/115; A63C 9/135
USPC .......... 2/67, 69, 82; 441/102, 103, 106–108, 441/112–119
See application file for complete search history.

(56) References Cited

U.S. PATENT DOCUMENTS

| | | | |
|---|---|---|---|
| 2,981,954 | A | 5/1961 | Garbellano |
| 3,134,994 | A | 6/1964 | Christofferson |
| D199,514 | S | 11/1964 | O'Neill |
| 3,771,169 | A | 11/1973 | Edmund |
| 4,293,957 | A | 10/1981 | Melarvie |
| 4,397,636 | A | 8/1983 | Ganshaw |
| 4,451,934 | A | 6/1984 | Gioello |
| 4,473,908 | A | 10/1984 | Knecht |
| 4,698,847 | A | 10/1987 | Yoshihara |
| 4,809,364 | A | 3/1989 | Lent |
| 4,862,517 | A | 9/1989 | Meistrell |
| 4,946,453 | A | 8/1990 | Monson |
| 4,999,845 | A | 3/1991 | Jenks, Jr. et al. |
| 5,013,271 | A | 5/1991 | Bartlett |
| 5,022,878 | A | 6/1991 | Casad |
| 5,052,053 | A | 10/1991 | Peart et al. |
| 5,165,110 | A | 11/1992 | Grilliot et al. |
| 5,191,658 | A | 3/1993 | Meistrell |
| 5,410,759 | A | 5/1995 | Hari |
| 5,509,142 | A | 4/1996 | Connell et al. |
| 5,630,229 | A | 5/1997 | Machado et al. |
| 5,768,703 | A | 6/1998 | Machado et al. |
| 5,809,567 | A | 9/1998 | Jacobs et al. |
| 5,898,934 | A | 5/1999 | Hunter et al. |
| 5,940,884 | A | 8/1999 | Grilliot et al. |
| 5,953,750 | A | 9/1999 | Stella |
| 6,202,216 | B1 | 3/2001 | Watanabe et al. |
| 7,017,195 | B2 | 3/2006 | Buckman et al. |
| 7,037,155 | B2 | 5/2006 | Freeman et al. |
| 7,059,925 | B2 | 6/2006 | Smith et al. |
| 7,125,302 | B2 | 10/2006 | Haselsteiner |
| 7,150,667 | B1 | 12/2006 | Leung |
| 7,233,829 | B2 | 6/2007 | Vlad |
| 7,460,886 | B2 | 12/2008 | Mazzarolo |
| 7,464,414 | B2 | 12/2008 | McDuff |
| D608,077 | S | 1/2010 | Bybee et al. |
| 7,992,218 | B2 | 8/2011 | O'Hara |
| 8,032,944 | B2 | 10/2011 | Demetropoulos |
| 9,572,378 | B2 * | 2/2017 | Canales ............... A41D 13/012 |
| 9,661,881 | B2 * | 5/2017 | Canales ............... A41D 13/012 |
| D800,995 | S | 10/2017 | Gatto et al. |
| 2001/0014981 | A1 | 8/2001 | Fairhurst et al. |
| 2002/0026664 | A1 | 3/2002 | Grounds et al. |
| 2003/0233694 | A1 | 12/2003 | Wescombe-Down |
| 2005/0101203 | A1 | 5/2005 | Kemp et al. |
| 2005/0241044 | A1 | 11/2005 | Zorica |
| 2006/0073749 | A1 | 4/2006 | Turner |
| 2006/0085889 | A1 | 4/2006 | Okajima |
| 2006/0230490 | A1 | 10/2006 | Okajima |
| 2006/0260018 | A1 | 11/2006 | Gordon et al. |
| 2007/0000015 | A1 | 1/2007 | Alaniz et al. |
| 2007/0028351 | A1 | 2/2007 | Coolik |
| 2007/0077126 | A1 | 4/2007 | Garcia et al. |
| 2007/0277278 | A1 | 12/2007 | O'Brien |
| 2007/0294797 | A1 | 12/2007 | Furgerson et al. |
| 2008/0141430 | A1 | 6/2008 | Rance et al. |
| 2009/0004938 | A1 | 1/2009 | Staver et al. |
| 2009/0038047 | A1 | 2/2009 | Di |
| 2009/0260125 | A1 | 10/2009 | Grilliot et al. |
| 2010/0212057 | A1 | 8/2010 | Sullivan |
| 2010/0225758 | A1 | 9/2010 | Mashiah |
| 2010/0269238 | A1 | 10/2010 | O'Hara |
| 2010/0299799 | A1 | 12/2010 | Belluye et al. |
| 2011/0035859 | A1 | 2/2011 | Koga et al. |
| 2011/0055746 | A1 | 3/2011 | Mantovani et al. |
| 2011/0151733 | A1 | 6/2011 | Gadler |
| 2011/0266314 | A1 | 11/2011 | Sommers |
| 2012/0011635 | A1 | 1/2012 | Tsuji et al. |
| 2012/0128425 | A1 | 5/2012 | Walck |
| 2012/0144541 | A1 | 6/2012 | Mitchell et al. |
| 2013/0042377 | A1 | 2/2013 | Moore et al. |
| 2013/0219579 | A1 | 8/2013 | Molyneux et al. |
| 2014/0313037 | A1 * | 10/2014 | Canales ............... A41D 13/012 340/573.1 |
| 2014/0338089 | A1 | 11/2014 | Brooks et al. |
| 2015/0082510 | A1 | 3/2015 | Inzer |
| 2015/0196072 | A1 | 7/2015 | Inzer |
| 2016/0262460 | A1 | 9/2016 | Inzer |
| 2017/0049159 | A1 * | 2/2017 | Canales ............... A41D 13/012 |
| 2017/0079339 | A1 | 3/2017 | Yeomans et al. |
| 2017/0215492 | A1 | 8/2017 | Canales et al. |
| 2017/0280791 | A1 | 10/2017 | Spenser et al. |
| 2017/0280792 | A1 | 10/2017 | Spenser et al. |

FOREIGN PATENT DOCUMENTS

| | | |
|---|---|---|
| GB | 2529472 A | 2/2016 |
| JP | 2005263116 A | 9/2005 |
| WO | WO-9959437 A1 | 11/1999 |
| WO | WO-2007038794 A2 | 4/2007 |
| WO | WO-2013082173 A1 | 6/2013 |

OTHER PUBLICATIONS

BarracudaUSA C1 Womens Comp Wetsuit. www.skylinenw.com. (2 pages) (Nov. 20, 2012).
Blue Seventy Axis Sleeveless Women's New Triathlon Wetsuit. www.wetsuitrental.com (2 pages) (Nov. 20, 2012).
Blue Seventy Wetsuits. www.intelligent-triathlon-training.com/blue-seventy.html. (3 pages) (Nov. 20, 2012).
Co-pending U.S. Appl. No. 15/790,706, filed Oct. 23, 2017.
Co-pending U.S. Appl. No. 15/791,754, filed Oct. 24, 2017.
Demerly. 2XU V:2 Wetsuit—A Collection of Valid Features. TriSports. com (9 pages) (Nov. 20, 2012).
PCT/US2012/066879 International Preliminary Report on Patentability dated Jun. 3, 2014.
PCT/US2012/066879 International Search Report dated Mar. 26, 2013.

(56) References Cited

OTHER PUBLICATIONS

Quintana Roo Neoprene Speed Sleeves. www.wetsuitrental.comlquintana-roo-speed-sleeve.html. (1 page) (Nov. 12, 2011).
Sammamish Valley Cycle. Triathlon Gear. (4 pages) (Nov. 20, 2012).
Slowtwitch.com. Product 2007. 2XU. (4 pages) (Nov. 20, 2012).
T:3 Team Wetsuit. www.2xu.com/product/731/T3-Team-Wetsuit./ 90. (2 pages) (Nov. 20, 2012).
U.S. Appl. No. 14/361,296 Office Action dated Sep. 1, 2016.
U.S. Appl. No. 15/346,654 Office Action dated Jan. 19, 2017.
U.S. Appl. No. 15/469,191 Office Action dated Jun. 1, 2017.
U.S. Appl. No. 15/471,895 First Action Interview dated Jul. 11, 2017.
U.S. Appl. No. 15/471,895 First Action Interview dated Jun. 2, 2017.
U.S. Appl. No. 15/484,707 First Action Interview dated Jun. 8, 2017.
Wetsuit Wearhouse. blueseventy. Men's Blue Seventy SPRINT Triathlon Wetsuit. (4 pages) (Nov. 20, 2012).
Definition of Buoyancy. The Physics Hypertextbook. Https://physics.info/buoyancy/summary.shtml (last referenced Feb. 27, 2018) (2 pgs).
Keeley. Open Cell vs. Closed Cell Foam: What's the Difference? CGR Products. Https://www.cgrproducts.com/open-cell-vs-closed-cell-foam (last accessed Feb. 27, 2018 (9 pgs).
U.S. Appl. No. 15/970,706 Office Action dated Jan. 30, 2018.
U.S. Appl. No. 15/791,754 Office Action dated Dec. 21, 2017.
Co-pending U.S. Appl. No. 15/951,812, filed Apr. 12, 2018.
amazon.com—De Soto Unisex T1 Black Pearl Pullover Wetsuit. Available at https://www.amazon.com/Unisex-Black-Pearl-Pullover-Wetsuit/dp/B009XGGW8G (4 pgs.) (Accessed Apr. 2018).
BT Forum—General Discussion: Beginner Triaathlete. Available at https://beginnertriathlete.com/discussion/forums/thread-view.asp?tid=163936&page=1 (7 pgs) (2009).
Desoto—learn About T1 Wetsuits. Available at https://www.desotosport.com/pages/learn-about-t1-wetsuits (7 pgs.) (Accessed Apr. 2018).
Desoto—T1 Wetsuits. Available at https://www.desotosport.com/collections/t1-wetsuits (14 pgs.) (Accessed Apr. 2018).
ebay.com—Desoto Wetsuit. Available at http://www.ebay.com/bhp/desoto-wetsuit (10 pgs.) (Accessed Apr. 2018).
Empfield. T1 by DeSoto. Available at http://www.slowtwitch.com/Products/Wetsuit_by_brand/T1_by_De_Soto/T1_by_De_Soto_4436.html (10 pgs) (2014).
Just Wetsuits—De Soto Unisex T1 First Wave Pullover. Available at https://www.justwetsuits.com/product/desoto-t1-first-wave-pullover/ (7 pgs) (Accessed Apr. 2018).
Slowtwitch—Trialthlon Forum. http://forum.slowtwitch.com/Slowtwitch_Forums_C1/Triathlon_Forum_F1/Clydesdale_wetsuit_dilema_P2115571/ (13 pgs) (2008).
Sporting Good 101. http://www.sportinggoods101.com/triathlon/triathlon-wetsuits/womens-wetsuits/full-sleeve-wetsuits/ (24 pgs) (Accessed Apr. 2018).
Swimoutlet—DeSoto T1 black Pearl Pullover Triathlon Wetsuit. https://www.swimoutlet.com/p/desoto-t1-black-pearl-pullover-triathlon-wetsuit-44542/ (5 pgs) (Accessed Apr. 2018).
Swimoutlet—DeSoto T1 First Wave Concept 5 Pullover Triathlon Wetsuit. https://www.swimoutlet.com/p/desoto-t1-first-wave-concept-5-pullover-triathlon-wetsuit-44550/ (4 pgs) (Accessed Apr. 2018).
The Bike Shoppe—Triathlon Wetsuit Rentals in Odgen, UT. Available at https://thebikeshoppe.com/about/ogden-utah-wetsuit-rentals-pg120.htm (4 pgs) (Accessed Apr. 2018).

\* cited by examiner

US 10,085,494 B2

SWIMWEAR DESIGN AND CONSTRUCTION

CROSS-REFERENCE TO RELATED APPLICATIONS

This application is a continuation of U.S. patent application Ser. No. 15/484,707, now U.S. Pat. No. 9,854,854, entitled "Swimwear Design and Construction" filed Apr. 11, 2017, which is a continuation of U.S. patent application Ser. No. 15/346,654, now U.S. Pat. No. 9,661,881, entitled "Swimwear Design and Construction" filed Nov. 8, 2016, which is a continuation of U.S. patent application Ser. No. 14/361,296, now U.S. Pat. No. 9,572,378, entitled "Swimwear Design and Construction" filed May 28, 2014, which is a U.S. National Stage Patent Application claiming priority to International Patent Application No. PCT/US2012/066879, entitled "Swimwear Design and Construction", filed Nov. 28, 2012, which claims priority from U.S. Provisional Patent Application No. 61/563,885 (Canales et al.), entitled "Swimwear Design and Construction, filed on Nov. 28, 2011, which are each incorporated herein by reference in their entireties.

FIELD OF THE DISCLOSURE

The present disclosure relates generally to swimming apparel, and more particularly to the design and construction of wetsuits and other swimwear.

BACKGROUND OF THE DISCLOSURE

Various wetsuits have been developed in the art, and are utilized for various purposes. Among these are performance wetsuits, which are popular among triathletes and open water swimmers. Performance wetsuits provide drag reduction in the form of faster-than-skin surface coatings, warmth and additional buoyancy to the wearer, and are designed to enhance the speed and ease with which the wearer moves through the water while swimming.

At present, a variety of performance wetsuits are currently available in the marketplace. These include those sold by Blueseventy, De Soto, Xterra, TYR and NeoSport. Most existing wetsuits are made primarily out of flexible neoprene.

SUMMARY OF THE DISCLOSURE

Figure 1:
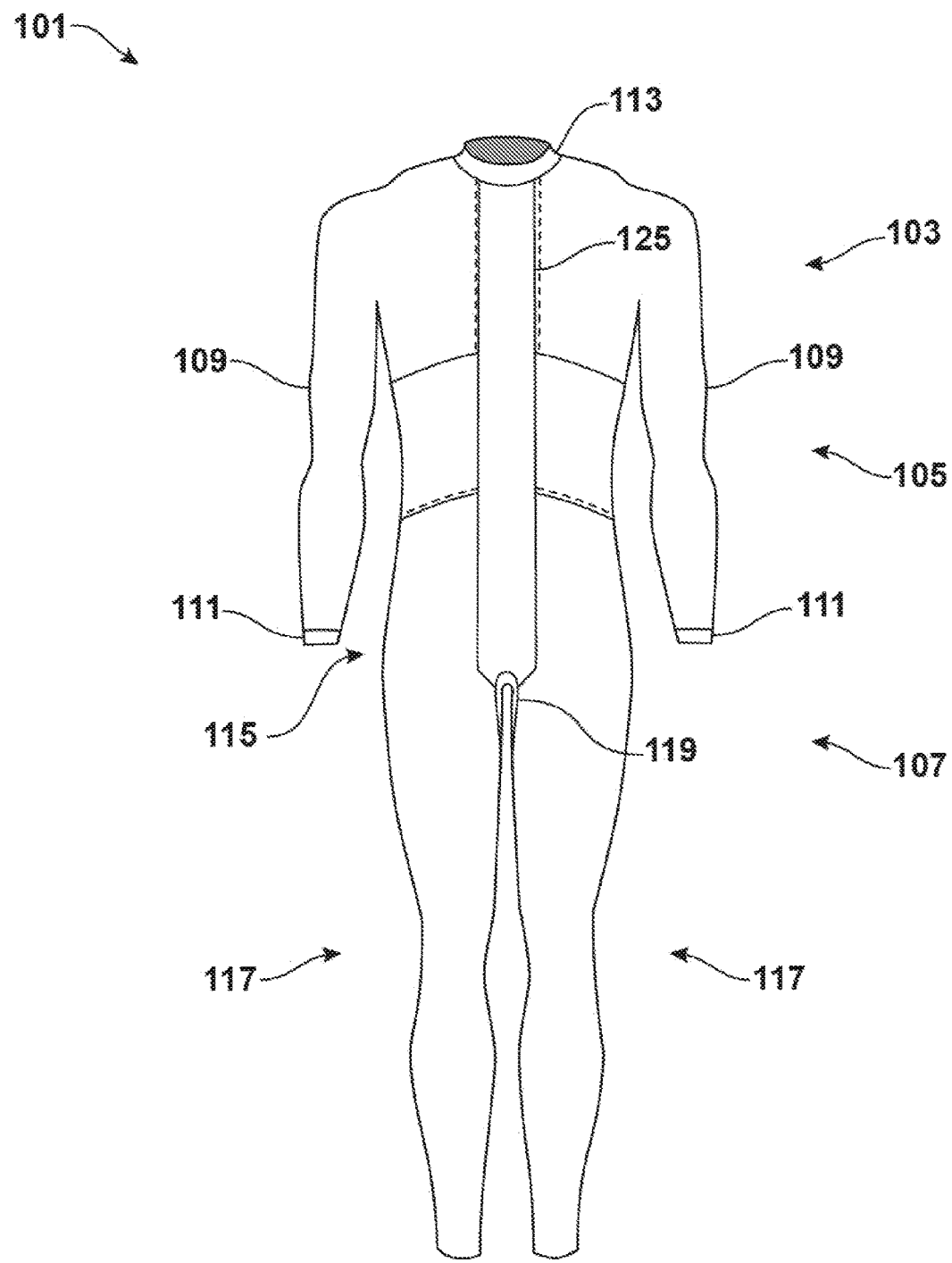
FIG. 1 is a front view of a first embodiment of a wetsuit in accordance with the teachings herein.

In one aspect, a wetsuit is provided which comprises (a) a first central region comprising a first material and having a first thickness; and (b) a second lateral region comprising a second material and having a second thickness; wherein the buoyancy per unit area of the first region is greater than the buoyancy per unit area of the second region.

In another aspect, a wetsuit is provided which comprises (a) a central region comprising a first material having a first density $\rho_1$; and (b) a lateral region comprising a second material and having a second density $\rho_2$; wherein $\rho_2 > \rho_1$.

In a further aspect, a wetsuit is provided which comprises a plurality of compartments, wherein each compartment has a thermally regulating device disposed therein.

In still another aspect, a method is provided for retrofitting a wetsuit with thermo-regulating devices, comprising: (a) providing a wetsuit; and (b) attaching a plurality of thermo-regulating devices to said wetsuit. In some implementations, the thermo-regulating devices may be connected to a system which may include, for example, goggles, a cap, a wristband, a watch, a heart rate monitor, or other such accessories.

In a further aspect, a wetsuit is provided which comprises a chest portion which covers the chest of a user; wherein said chest portion is equipped with a zipper. In a similar aspect, a wetsuit is provided which comprises a back portion which covers the back of a user; wherein said back portion is equipped with a zipper.

In another aspect, a wetsuit is provided which comprises (a) a resilient portion of fabric which fits around the body of a user, thus defining an interior space at least partially occupied by the body of the user, and an exterior space external to said resilient portion of fabric; (b) a one-way valve which provides a fluidic flow from the interior space to the exterior space; and (c) an actuator which opens the valve.

In a further aspect, a wetsuit is provided which comprises (a) a vest; and (b) pants, integrally attached to said vest; wherein said vest and pants comprise a foamed polymeric material.

In still another aspect, a sleeve is provided in combination with a wetsuit. The sleeve comprises (a) a first portion having a first thickness which covers the medial portion of a user's forearm; (b) a second portion having a second thickness which covers the medial portion of a user's bicep; and (c) a third portion having a third thickness which extends across the lateral portion of a user's arm, from the wrist to the triceps; wherein said second and third portions comprise a foamed polymeric material, and wherein said third thickness is greater than said second thickness.

DETAILED DESCRIPTION

As used herein, the term "aerated neoprene" refers to a type of neoprene which comprises multiple laminated layers, at least one of which is perforated and cut such that the final product is a sealed neoprene with individual pockets of air trapped inside the neoprene layers.

While existing wetsuits may be suitable for their intended purpose, a need exists for further improvements in the art. This is especially so with respect to performance wetsuits that are designed for use in swimming and triathlon events, since even small improvements in such wetsuits can make the difference between success or failure for the wearer. This point is illustrated by the fact that some recent Ironman triathlons have been decided by a few seconds, even though these competitions typically last more than 8 hours. For example, the 2012 Ironman Cozumel triathlon's female race was won by seven seconds, after a total elapsed time of nine hours and fifteen minutes.

One area requiring improvement in wetsuits, especially those designed for swimmers, relates to the density and thickness of the foamed polymeric materials (typically neoprene) used in their construction. In particular, some wetsuits do not impart optimal buoyancy to the wearer, due to the density and thickness of the neoprene used in their construction. This causes the wearer to ride lower in the water, thus reducing swimming speeds and increasing energy expenditure. In some cases, suboptimal placement may also cause the swimmer to ride too high in the water in the chest. This causes the legs to drop, thus resulting once again in a suboptimal net body position.

Other wetsuits incorporate lower density neoprene into them in a bid to improve buoyancy. However, the density distribution in such wetsuits is typically suboptimal, and leads to increased heat retention and resistance to proper swimming mechanics. For example, such designs often incorporate lower density materials into the arms and hips of the wetsuit, which may inhibit the proper rotation of the swimmer's body along its longitudinal axis (roll). Similarly, such designs also often fail to ensure optimal body position along a lateral axis (pitch).

It has now been found that the foregoing issues may be addressed through the use in the construction of a wetsuit of a foamed polymeric material having variable density and thickness. Buoyancy (also known as the buoyant force), is the upward force exerted on an object that is wholly or partly immersed in a fluid. The magnitude of the buoyant force on an object is equal to the weight of the fluid it displaces. Buoyancy is caused by differences in pressure acting on opposite sides of an object immersed in a static fluid. Objects immersed in a fluid have an apparent weight that is: 1) reduced by the buoyant force (less than their actual weight) and 2) directly proportional to the relative density. Relating buoyancy to density: When the density of the object is less than the fluid, the object rises in the fluid. When the density of the object is equal to the density of the fluid, the object has neutral buoyancy. When the density of the object is greater than the fluid, the object sinks in the fluid. In particular, the placement, density and/or thickness of the neoprene or other foamed polymeric material may be varied to optimize the buoyancy distribution (as, for example, by making the central portion of the wetsuit more buoyant than the lateral portion to facilitate rotation or roll along the longitudinal axis) and body position along the lateral axis (pitch) of the user. This approach has the effect of enhancing proper swim mechanics, including the proper rotation of the user's body along its longitudinal axis. This enhancement is of particular value, because proper swimming technique requires rotation of up to 40 degrees in each direction on the longitudinal axis. Similarly, the proper alignment along the lateral axis (pitch) leads to a reduction of form drag. Hence, this approach helps to optimize buoyancy for the swimmer along the latitudinal axis, while simultaneously facilitating proper rotation along the longitudinal axis.

A further area requiring improvement in existing wetsuit designs, especially for swimmers, relates to the sleeve design of wetsuits. At present, most wetsuit designs treat the shoulder and sleeve areas of the wetsuit like any other area. Consequently, these areas are typically constructed out of the same neoprene material as the rest of the suit, with the result that the wetsuit in general, and these areas in particular, are uniform in neoprene type, density, and thickness.

However, the art has failed to appreciate that it is both unnecessary and undesirable to have neoprene on the shoulder areas of the wetsuit, since the use of neoprene in this area merely heats up muscles that are doing most work of the work in a swimming event, and restricts the swimmer's range of motion. While some companies, such as Quintana Roo (Chattanooga, Tenn.), have sold "speed sleeves" (see, e.g., http://www.wetsuitrental.com/quintana-roo-speed-sleeve.html) which, as a standalone device, leave the shoulders uncovered, these solutions are uniform in neoprene type, density, and thickness, and hence do not consider the effect of the distribution of neoprene thickness and density on proper stroke technique and buoyancy.

It has now been found that the thickness of the neoprene or other foamed polymeric material from which wetsuits are typically fabricated may be manipulated to create a sleeve which optimizes proper stroke technique and buoyancy. In a preferred embodiment, the sleeve utilizes (a) textile or thin neoprene at a first thickness (preferably 1-2 mm) on the medial forearm area, upon which is laminated one or more layers of silicone or other textured material to increase resistance during the "catch" or "pull" phase of the swim stroke, (b) textile or thin neoprene at a first thickness (preferably 1 mm or less) in the elbow and crook or in an articulated panel design, (c) neoprene at a second thickness (preferably 3-5 mm) in the bicep area, and (d) neoprene at a third thickness (preferably at least about 5 mm and of aerated or open cell neoprene form) in the form of a strip on the lateral portion of the forearm extending from the wrist through the triceps. The sleeve also preferably utilizes in the forearm and/or or the bicep and tricep neoprene or textile laminates with muscle compression technology (most commonly found in the form of a special textile weave), the purpose of which is to reduce fatigue and encourage venous blood flow during exercise.

In addition, the maximum allowable (currently 5 mm) thickness of neoprene under various triathlon and swimming governing bodies is preferably used down the centerline of the wetsuit and inside of the legs to promote buoyancy along the lateral axis (pitch) and enhanced rotation along the longitudinal axis (roll) of the swimmer's body. The neoprene selection for this portion is preferably aerated neoprene, such as that sold by the Yamamoto Corporation under the trade name AERODOME™. This neoprene selection helps to optimize buoyancy while complying with appropriate thickness regulation(s). Since some aerated neoprenes do not conform well to the natural curvature of the lower back, it is preferred in some embodiments that aerated neoprene is only used on the front of the wetsuit.

A coated textile or another thin material with less buoyancy is used in a strip about 2-3 inches wide down the outside of the wetsuit to promote rotation along the longitudinal axis of the user's body and to promote rotation and allow heat to escape from the suit. This feature also makes entry and removal of the suit easier and faster, which is critical for the timed sport of triathlon, where athletes must exit the water and quickly remove swimwear before proceeding to the next discipline, cycling. Non-aerated 5 mm closed cell neoprene may be used in between the centerline. Neoprene of a lesser thickness, preferably about 2 mm to about 3 mm, is used from the naval up (excluding the centerline, which preferably has a thickness of 5 mm or the maximum allowable under said governing bodies) to create and compensate for the buoyancy differential between the chest and legs along the lateral axis (pitch). The use of more rigid neoprene in the torso area also provides structural support to the abdominals and other core muscles, which can tire prematurely during swimming. Preferably, the most flexible neoprene is reserved for the chest, back, shoulder and arm panels, where maximum range of motion is desired.

It will be appreciated from the foregoing that some of the wetsuits disclosed herein utilize variable rigidity to optimize certain characteristics of the wetsuit. In particular, in some embodiments, the wetsuits disclosed herein are constructed to have some rigidity in certain locations, such as along the center line and along the sides of the torso. Some embodiments of these wetsuits may be further equipped with one or more additional strips, disposed directly on the side of the torso between the hip and the middle of the rib cage, that are even more rigid to prevent "snaking" when swimming. Moreover, some embodiments may contain relatively more elastic or rigid neoprene on the back of the suit to prevent the swimmers arms from over-extending during the entry and extension phase of the freestyle stroke, helping to promote proper technique.

In some variations of the foregoing embodiment, various types of "treads" may be utilized in the forearm area to optimize the "catch" and "feel" of the swimmer's stroke. Preferably, this includes a "graded" catch panel that enhances propulsion by creating additional surface area and resistance on the forearm. Moreover, the foregoing features may be implemented in a full wetsuit (with sleeves) or in a "hybrid" configuration with a long john (no sleeves) and separate swim sleeves.

Another area requiring further improvement in existing wetsuit and swimwear designs—especially those intended for use by triathletes and other competitive swimmers—relates to the user's body temperature. Conventional wetsuits are typically constructed from neoprene and other thermally insulating materials. Consequently, users can overheat (or experience the sensation of overheating) in such wetsuits, even when swimming at submaximal (e.g., below lactate threshold or aerobic threshold) effort levels. Such overheating may lead to premature fatigue and dehydration. A similar problem may be encountered with textile-based wetsuits or other swimwear.

It has now been found that this problem may be addressed by incorporating cooling packs or other thermoregulation devices into the wetsuit or swimwear. In addition to actually cooling and temperature regulation of muscle and veins, the provision of such devices also treats the mind and the nervous system.

In a preferred embodiment, the thermoregulation devices may take the form of thin neoprene or textile pouches which contain cooled, frozen or instant gel packs (the latter of which may be automatically or manually activated prior to or during exercise), and which affix to (or are defined in) the inside of the wetsuit or other swimwear. The gel packs may assume different shapes and sizes, based on their location in the swimwear.

In some variations, the gel packs may be laminated to the swimwear, or might be configured to be used without the provision of pouches, pockets or compartments in the swimwear. In particular, the thermoregulation devices may be fabricated as separate, removable constructs that can be sold as add-on products for swimwear that are not equipped with thermoregulation devices. In some embodiments, the swimwear may also incorporate systems that monitor temperature, circulate fluid, or create specific temperature regulated spots on certain parts of the suit to achieve the intended thermoregulatory effect.

Another area requiring further improvement in existing wetsuit design, especially for swimmers, relates to the manner in which the wetsuit is secured around the body of a user. In a conventional wetsuit, a zipper is provided on the back of the suit for this purpose. The use of a zipper is convenient in that it allows the user to change into and out of the wetsuit quickly and easily. However, the disposition of the zipper on the back of the suit is a legacy from surfing and bodyboarding wetsuits, where it is desirable to minimize any abrasion on the chest that could result from repeated contact with a surfboard or bodyboard.

It has now been found that the use of wetsuits by competitive swimmers may be enhanced by disposing the zipper on the front (or, in some embodiments, on the side or at an angle sweeping from the front to the side) of the wetsuit. This disposition of the zipper allows for easier, faster, and less energy-consuming entry and exit from the suit, which is a significant advantage in competitive events such as triathlons, where a transition from the swim portion of the race to the cycling portion of the race typically takes minutes. This disposition also offers better access to the thermoregulation pouches in the chest and any electronic devices that may be integrated into the suit. While it may be desirable in surfing and bodyboarding wetsuits to minimize any abrasion on the chest that could result from repeated contact with a surfboard, no such constraints exist in swimming applications.

Moreover, the disposition of the zipper on the front of the wetsuit reduces fabric bunching at or near the base of the neck. Such bunching tends to occur, for example, when the user looks up to sight a line of navigation while swimming, as is common in triathlon races that involve a polygonal swim course defined by multiple floating buoys. This issue is especially problematic in triathlon swimming, because such bunching lets in water and air, which can be uncomfortable and can alter body position and buoyancy characteristics, and which can lead to chafing of the neck.

Some companies have attempted to address this issue by over-engineering a large neoprene flap in this area and by using releasable fasteners such as the hook and loop type fasteners marketed under the trade name VELCRO™, but these provisions do not adequately address the problem. In fact, this approach may create more bunching and may actually make it harder for the swimmer to lift his or her head, due to the increased mass of the flap. Additionally, adding a flap and additional material to the back of the neck increases drag, which further limits performance. Moreover, such a flap may cause significant drag for suits that are often sold with very expensive, special coatings touted to marginally minimize drag coefficients. By contrast, with the zipper disposed in the front of the wetsuit, such bunching may be reduced, the water/air seal may be improved, drag is reduced, and it is easier for the swimmer to lift his or her head to sight a buoy, the coastline, or other reference point required for navigation.

A further area requiring improvement in existing wetsuit designs, especially for swimmers, relates to the formation or presence of air bubbles or water in the suit during use. In particular, air bubbles are often created in the lower back portion of the wetsuit. The wetsuit may also take on water or air due to the natural arch in a user's back, or due to suboptimal neoprene panel design.

It has now been found that the foregoing problems may be dealt with through the provision of a one-way air and/or water release valve in the wetsuit. Such a valve provides the means by which trapped air or water may be removed from the suit, without causing the suit to take on additional air or water. The valve may be manually activated by the user, or may be activated automatically by a monitoring system or by other means. A simple valve may be created by using two layers of neoprene with offset holes, such that air passes from one set of interior holes out into a chamber that then has a single escape hole. Alternatively, an engineered valve may be built and integrated into the suit. Such valve preferably has a low-profile and is relatively flat to minimize drag in the water. One or more valves may be place in the suit to remove one or more pockets of air. For example, two valves may be placed, individually, on either side of the rear zipper. Alternatively, a single valve may be placed just below the base of the rear zipper. In a wetsuit embodiment that contains a front zipper instead of a rear zipper, one or more valves could be placed directly on the rear centerline of the suit.

Still another area requiring improvement in existing wetsuit and swimwear designs relates to proper hydration of the wearer. Many competitive events featuring a swimming component require contestants to spend a considerable amount of time in the water. For example, the swimming portion of the Ironman competition is a 2.4 mile race. Even for excellent swimmers, this distance can take an hour or longer to complete. Moreover, many races take place in relatively warm water and warm ambient temperatures, where dehydration can become a concern. Dehydration and improper nutrition are the enemies of a triathlete, and the swim is the start of a multi-hour effort. Swimming in warm water, or in a hot wetsuit or other overheating swimwear, may significantly increase the chance of dehydration.

It has now been found that this issue may be dealt with through the provision of a pouch that allows insertion of a hydration bladder, a nutrition compartment, or both. This pouch may be disposed, for example, on the chest or back panel(s) down the centerline. In some variations, the bladder may be laminated to the swimwear, or might be configured to be used without the provision of pouches, pockets or compartments in the swimwear. In particular, the bladder may be fabricated as a separate, removable construct that can be sold as add-on products for swimwear that is not equipped with a bladder or pouch.

In some embodiments, the bladder or compartment may be equipped with a one-way valve or other such means to prevent it from taking on air and thus becoming a buoyancy aide. This may allow the device to comply with USAT and WTC rules that prohibit the use of floaties or other devices that aide buoyancy, since the valve would serve to make the hydration bladder buoyancy neutral by keeping it full of liquid or keeping it empty. Of course, it will be appreciated that these provisions may not be necessary if, for example, the swimwear is to be used merely as a "training" suit.

Another area requiring improvement in existing designs for wetsuits and other swimwear relates to the integration of technology into the swimwear, and GPS technology in particular. Triathletes frequently use GPS to track their performance on the swim, bike, and run portions of a triathlon, but many athletes do not want to wear a bulky watch while swimming, or attach an add-on externally. Furthermore, GPS tracking can also function as a safety precaution in races, training, and recreational swimming. Existing GPS technology limits the accuracy of the swim data. In particular, although some advances have been made in the use of software to smooth the spikes in the GPS swim readings that come from losses in signal, this is achieved through computational guesses, and hence the results may not reflect the swimmer's actual course through the water. Some swimmers have attempted to place their GPS watches inside of their latex or silicone swimming caps, in the hopes of keeping the GPS device above water, to improve the reception. However, bulky watches can shift in the swimming cap and can be both noticeable and uncomfortable.

It has now been found that this issue may be dealt with through the integration into the swimwear of a GPS antenna/receiver, through construction of the suit or the inclusion of a pouch, which may connect or pair with a tracking device to increase the GPS signal reception. The antenna/receiver (which may comprise, for example, wires that run through or along the surface of the back of the swimwear and a waterproof hardwire cable connection that can interface with a GPS device) may be designed as a proprietary device, but may also be configured to be compatible with third-party receivers using a suitable adapter in a wired or wireless configuration. The antenna/receiver may also connect to a receiver via wireless transmission using various commercial protocols such as, but not limited to, ANT+ and Bluetooth™.

Yet another area requiring improvement in existing designs for wetsuits and other swimwear relates to the cadence of the swimmer's stroke. In distance swimming, it is important to maintain an even cadence and distance per stroke to maintain a consistent pace and physical effort. This issue is of tremendous importance in a multi-hour event that is largely completed at an aerobic effort level, such as a long distance triathlon or open water swim race. Moreover, in competitive swimming events such as triathlons, it is easy to get distracted, thus causing the swimmer to lose cadence or distance per stroke and become fatigued.

It has now been found that this issue may be dealt with through the integration into the swimwear of one or more cadence sensors to relay cadence information to swimmer. In a wetsuit, this may take the form, for example, of accelerometer sensors built into the forearms of the wetsuit, which may use appropriate radio signals or hardwiring to relay cadence data to a central computing system (which may or may not be integrated into the wetsuit). In some embodiments, the arms of the wetsuit may contain LED panels that alert the swimmer with colors or light patterns when predefined cadence goals are met. Other embodiments may contain a vibration mechanism that alerts the swimmer when certain goals are no longer being achieved, or when the cadence of the swimmer has deviated undesirably. Still other embodiments may utilize LEDs to signal distance completion, especially when used in coordination with a GPS system. Such a configuration is of value because it is difficult for a swimmer to know where he or she is distance-wise during a 2.4 mile swim. Variations of this embodiment may utilize audio cues, either in place of or in addition to LED signals. In other embodiments, cadence sensors may be disposed in the ankles of the wetsuit to monitor the strength of the kick, since a steady kick is important for both stabilization and propulsion. Of course, it will be appreciated that the foregoing features may be implemented in types of swimwear other than wetsuits.

Another area requiring improvement in existing designs for wetsuits and other swimwear relates to the heart rate of the swimmer. In competitive swimming events such as triathlons, it is easy to get excited or anxious in a race and swim too fast or too hard at points in the race. For example, many triathlons have "mass swim starts" that involve hundreds or thousands of athletes starting the swim in a large group. This may lead to a premature rise in heart rate that causes undesired fatigue. This issue is of critical importance in long distance triathlons, which are often completed over multiple hours and raced at aerobic effort levels.

It has now been found that this issue may be dealt with through the integration into the wetsuit or other swimwear of a heart rate monitor to give a swimmer in-water feedback on heart rate. This may be accomplished, for example, through the use of pre-existing heart rate monitor chest, ear and/or wrist strap technology to monitor heart rate metrics and to relay data to a central computing system (which may or may not be integrated into the wetsuit). The swimwear may be adapted to vibrate or otherwise alert the swimmer when pre-defined heart rate goals are met, lost or deviated from. In some embodiments, the heart rate monitor may be integrated with an LED, fiber optic or other visual indicator system to provide visual alerts, or with an audio system to provide audio alerts.

Still another area requiring improvement in existing designs for wetsuits and other swimwear relates to the performance metrics of the swimmer, such as heart rate. It is very difficult to track overall performance and metrics while swimming, especially while racing.

It has now been found that this issue may be dealt with through the integration into the swimwear of a performance feedback monitoring system to give athletes convenient access to key performance and health data while they are training and competing. Such data may include, but is not limited to, heart rate, cadence, distance, direction, speed and body temperature. This may be accomplished, for example, through the use of thin, hydrodynamic wrist units, ear buds for audio communication, or heads-up display goggle units that communicate with various sensors and monitoring systems built into the swimwear. Such systems may also integrate with the swimmer's cap, which is a required piece of equipment in triathlons and which could serve as a storage location and a "bridge" between the goggle system and the suit.

FIGS. 1-4 depict a first particular, non-limiting embodiment of a wetsuit in accordance with the teachings herein. The wetsuit 101 depicted comprises a top portion 103, a middle portion 105 and a bottom portion 107. The top portion 103 extends around the shoulders and chest of the wearer, and includes sleeve portions 109 that extend down the arms of the wearer. Each of the sleeve portions 109 terminates in a cuff 111. The top portion 103 terminates at one end in a collar 113 which extends around the neck of the wearer, and terminates at the other end at the middle portion 105.

The bottom portion 107 includes a waist portion 115 that extends around the waist of the wearer, leg portions 117 that extend down the legs of the wearer, and a crotch portion 119.

Figure 2:
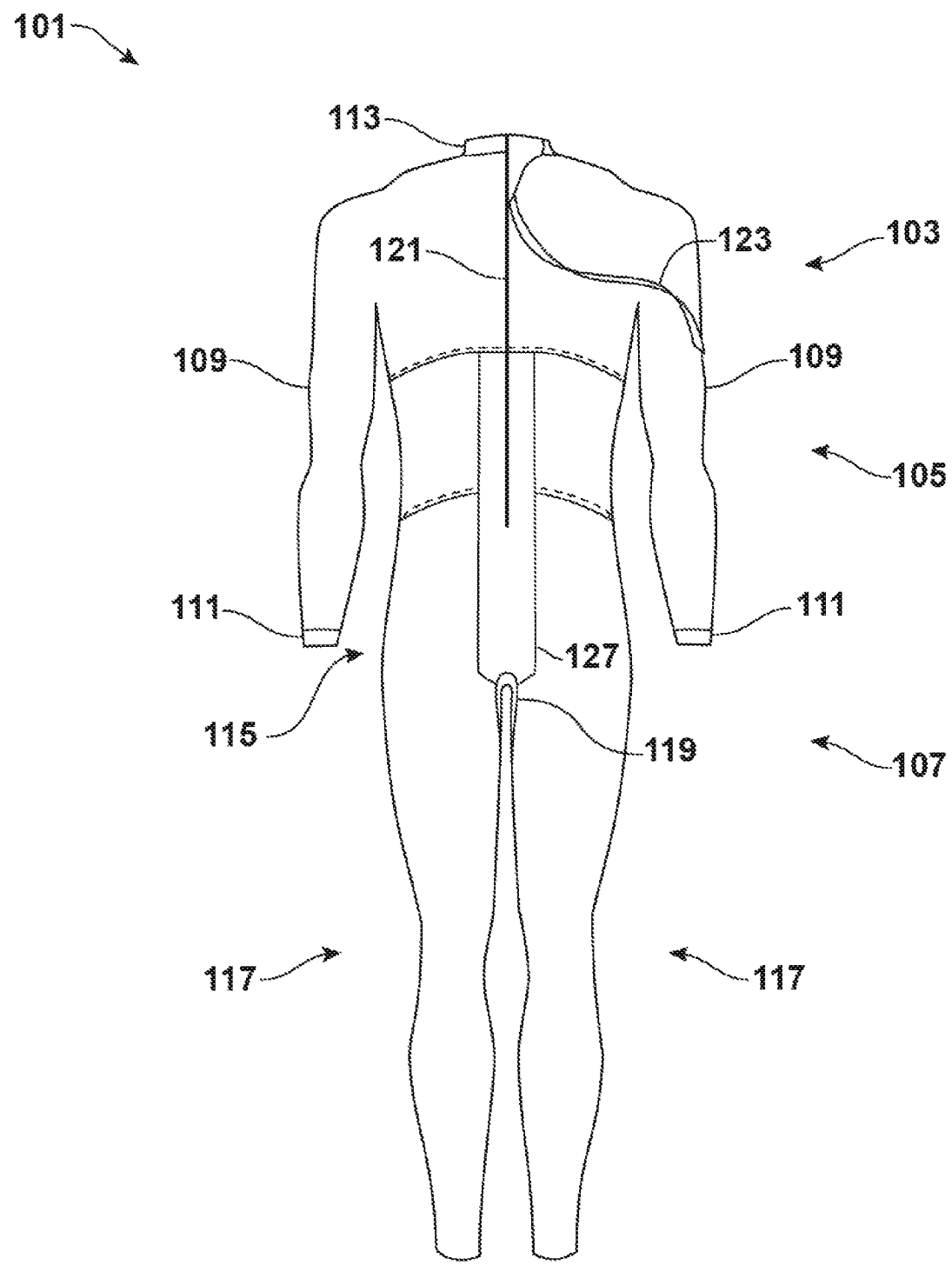
FIG. 2 is a rear view of the wetsuit of FIG. 1.
Figure 3:
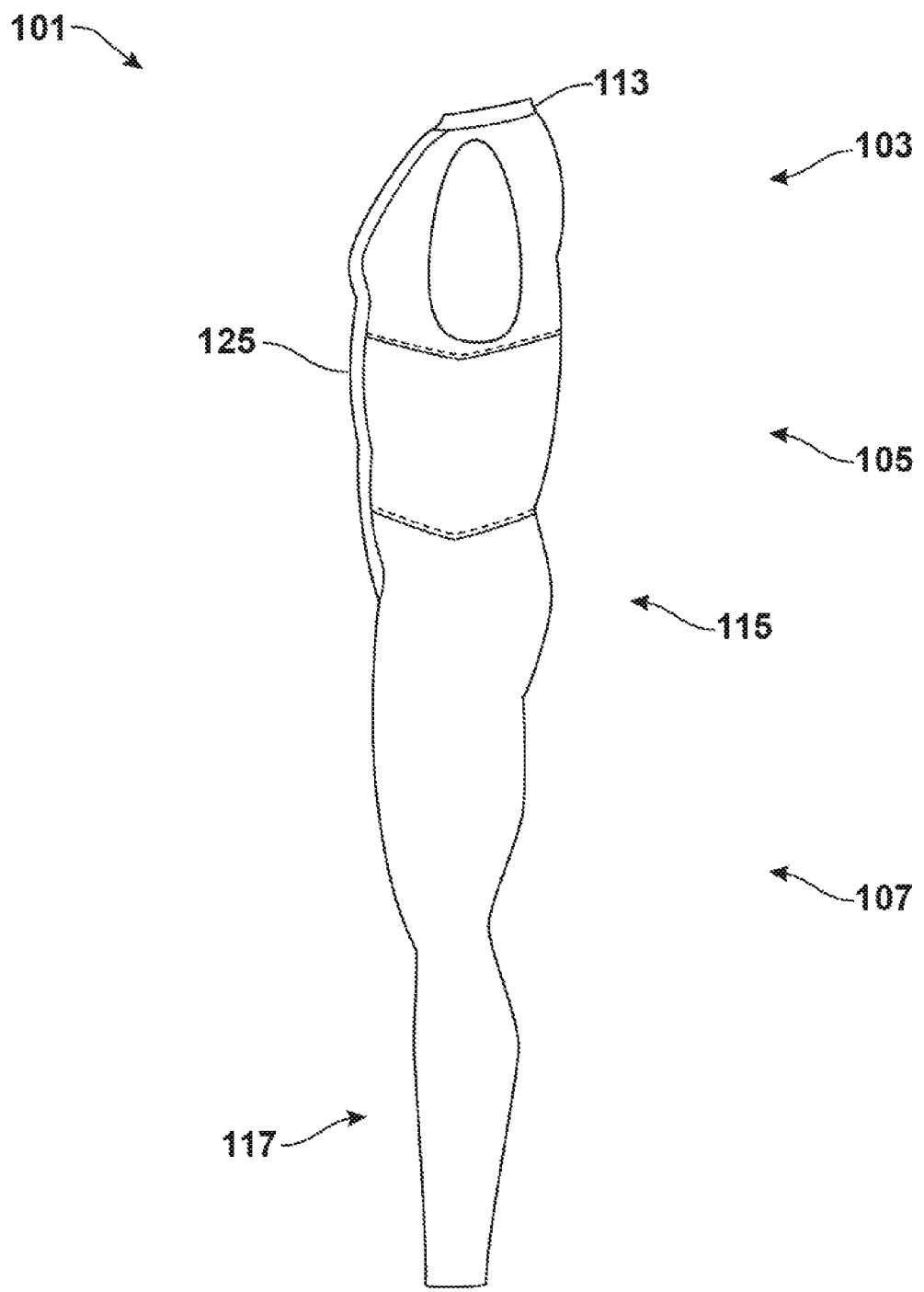
FIG. 3 is a side view (left side) of the wetsuit of FIG. 1; the left arm has been removed for clarity of illustration.
Figure 4:
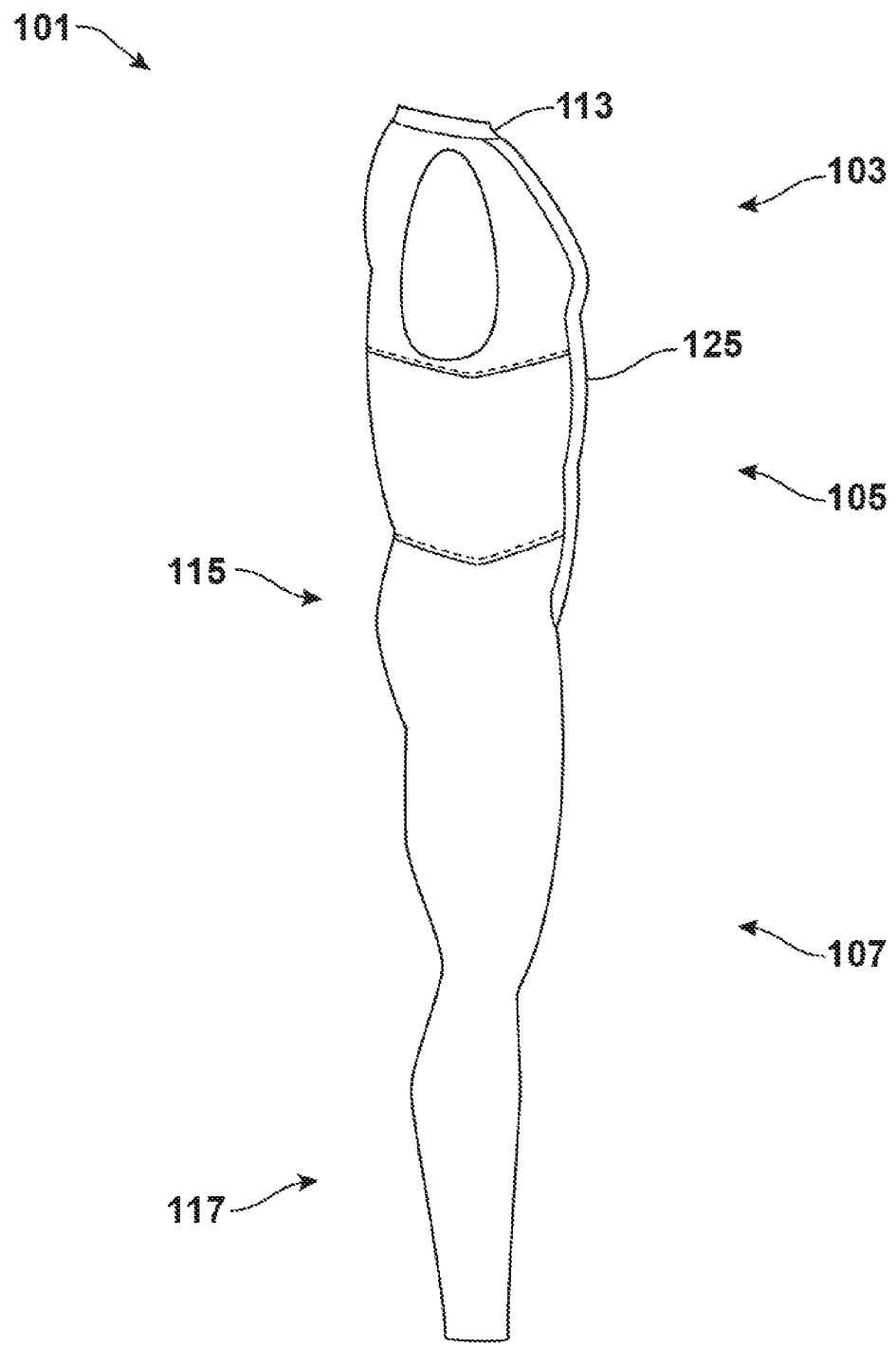
FIG. 4 is a side view (right side) of the wetsuit of FIG. 1; the right arm has been removed for clarity of illustration.
Figure 5:
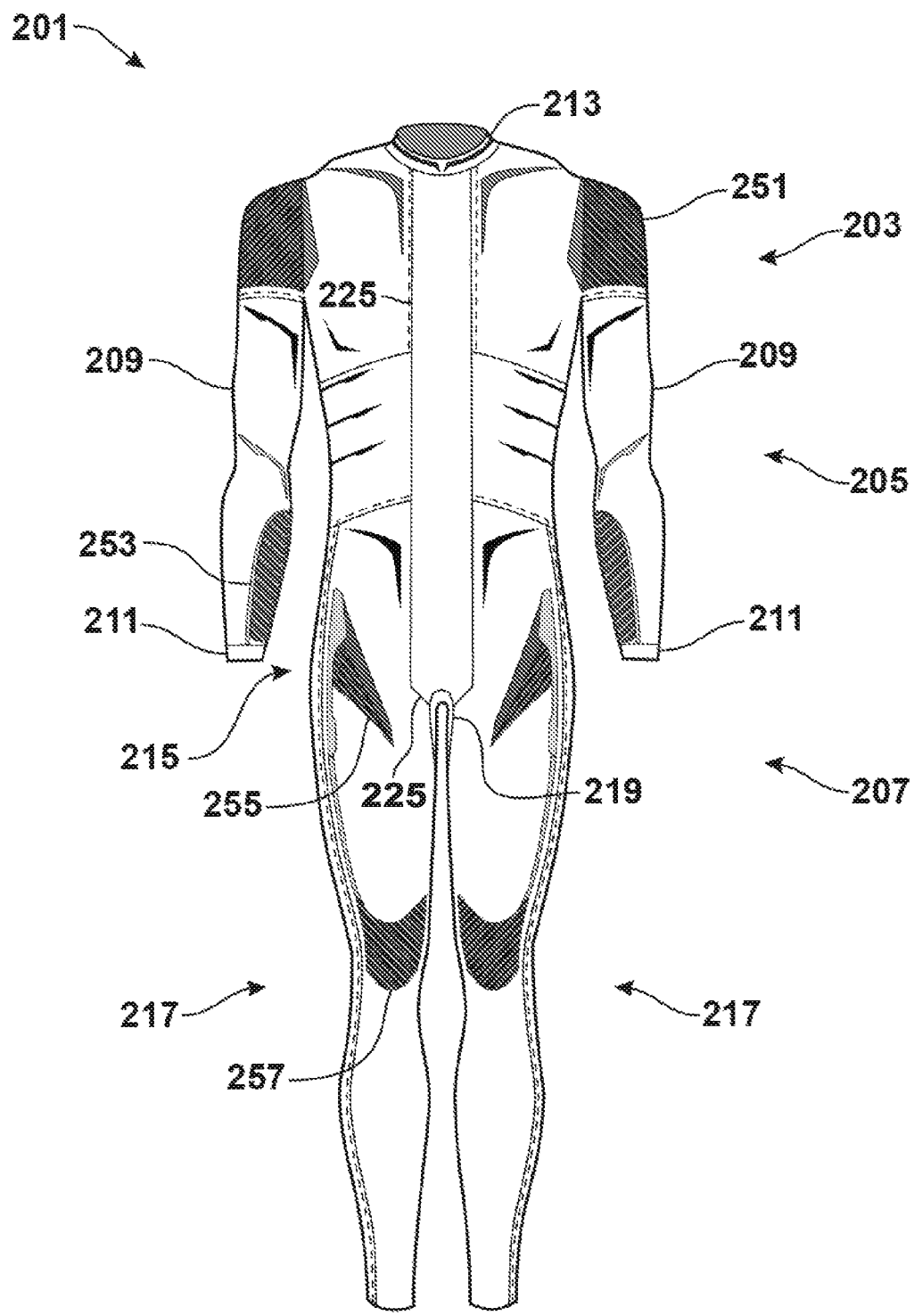
FIG. 5 is a front view of a second embodiment of a wetsuit in accordance with the teachings herein.

As seen in FIG. 2, the wetsuit 101 is equipped with a zipper 121 that extends down the back of the wetsuit 101 from the collar 113 to the bottom portion 107. A strap 123 is provided which allows the wearer to zip and unzip the wetsuit without help.

A first buoyancy enhancer 125 (see FIG. 1) is provided on the front of the wetsuit 101 in the form of a strip which extends from the collar 113 to the crotch 119. Similarly, a second buoyancy enhancer 127 (see FIG. 2) is provided on the back of the wetsuit 101 in the form of a strip which extends from the intersection between the top 103 and middle 105 portions to the crotch 119. In some embodiments, the second buoyancy enhancer 127 may comprise a different (and preferably more flexible) material than the first buoyancy enhancer 125 to allow the wetsuit to better follow the curvature of the lower back.

In use, the buoyancy enhancers 125, 127 provide additional buoyancy in the center of the wetsuit 101 along the longitudinal axis of the wearer's body. Without wishing to be bound by theory, the additional buoyancy is believed to allow the wearer's body to ride higher in the water during swimming, thus reducing the resistance encountered by the wearer by reducing the amount of surface area of the wearer's body which is in contact with the water. Reduction of buoyancy in the chest and back panels on either side of the centerline reduces mass in the chest. When coupled with the relatively greater buoyancy in the legs, the wetsuit puts the swimmer's body in a neutral body position. Without such equalization, the body's natural floatation source (the lungs) would cause the swimmer's chest to float too high in the water relative to the hips and legs, causing form drag. A proper, neutral body position in swimming is colloquially known as "swimming downhill," because it creates the sensation of swimming downwards. This position is actually ideal, and provides the least amount of form drag.

Moreover, the placement of the additional buoyancy along the longitudinal axis of the wearer's body is believed to provide for better rotational stability, decreased resistance during a normal swim stroke (such as a traditional free style stroke), and improved balance. By contrast, some prior art swimsuits which are equipped with buoyancy enhancers have the buoyancy enhancers disposed along the hips and/or arms and legs of the wetsuit. Such designs create imbalance and rotational instability during a normal swim stroke. Moreover, such designs increase the resistance encountered by the user by increasing the buoyancy of the user's arms and legs as they move through the water.

FIGS. 5-9 depict a second particular, non-limiting embodiment of a wetsuit in accordance with the teachings herein. The wetsuit 201 depicted comprises a top portion 203, a middle portion 205 and a bottom portion 207. The top portion 203 extends around the shoulders and chest of the wearer, and includes sleeve portions 209 that extend down the arms of the wearer. Each of the sleeve portions 209 terminates in a cuff 211. The top portion 203 terminates at one end in a collar 213 which extends around the neck of the wearer, and terminates at the other end at the middle portion 205.

The bottom portion 207 includes a waist portion 215 that extends around the waist of the wearer, leg portions 217 that extend down the legs of the wearer, and a crotch portion 219.

Figure 6:
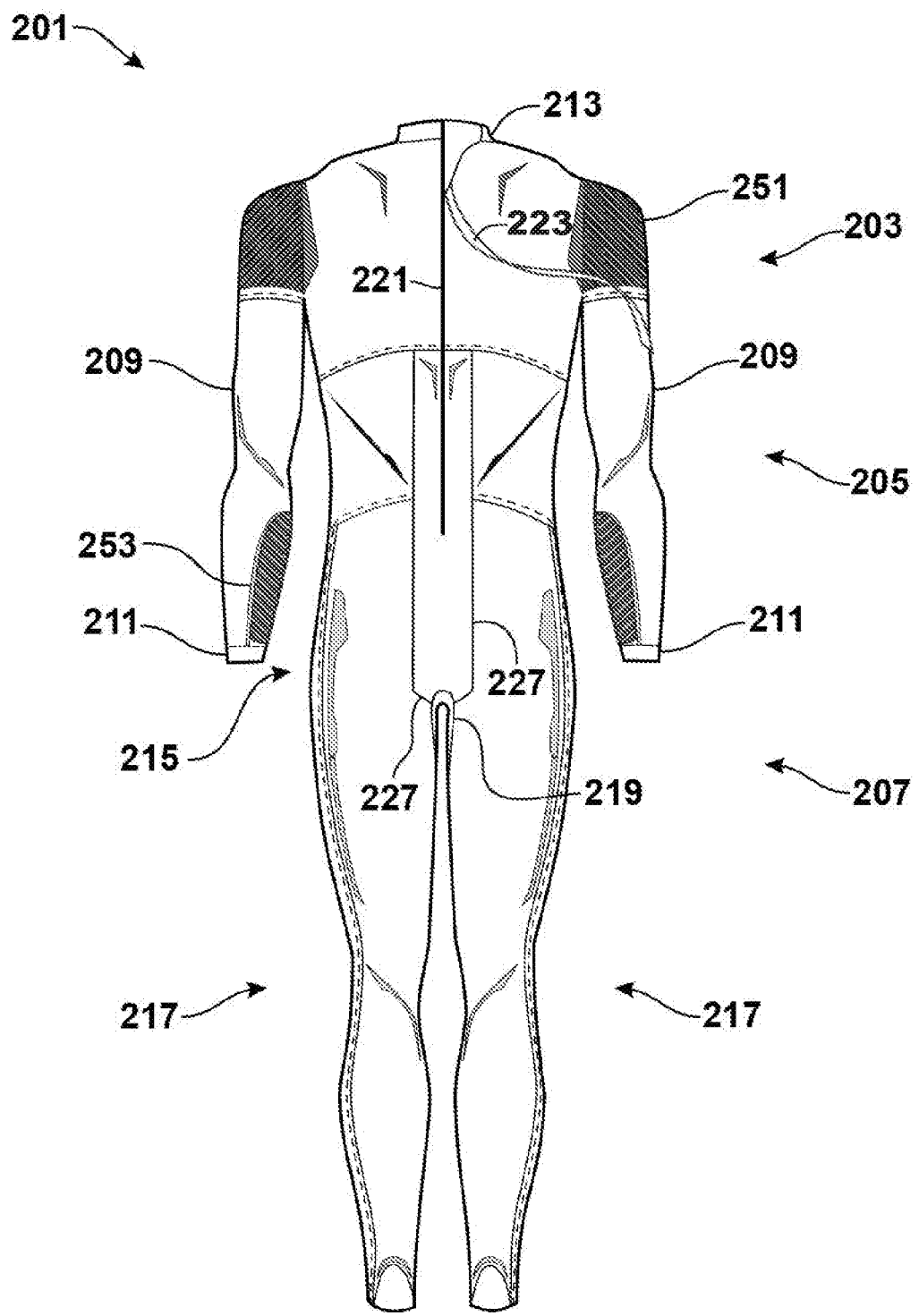
FIG. 6 is a rear view of the wetsuit of FIG. 5.
Figure 7:
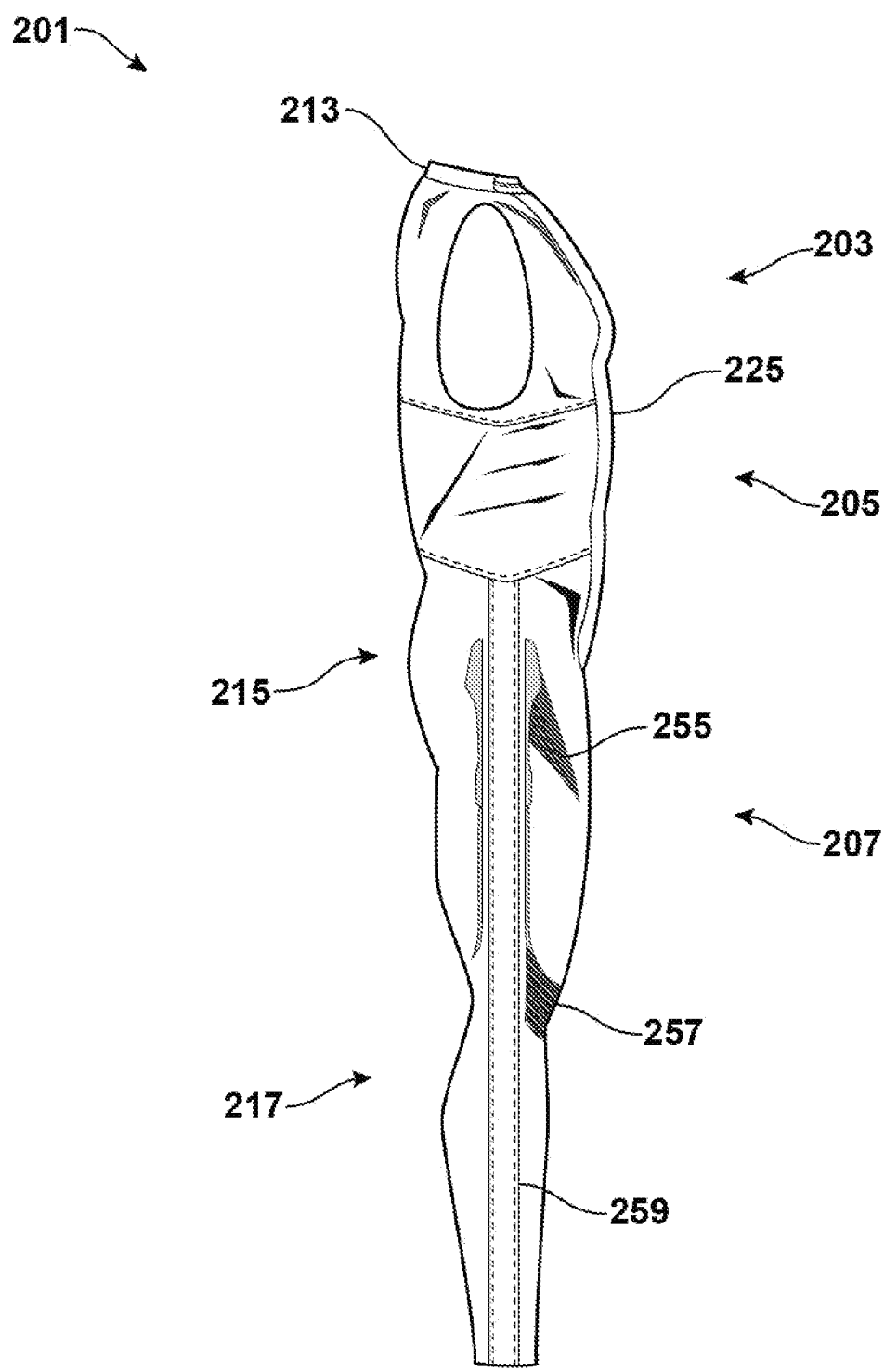
FIG. 7 is a side view (right side) of the wetsuit of FIG. 5; the right arm has been removed for clarity of illustration.
Figure 8:
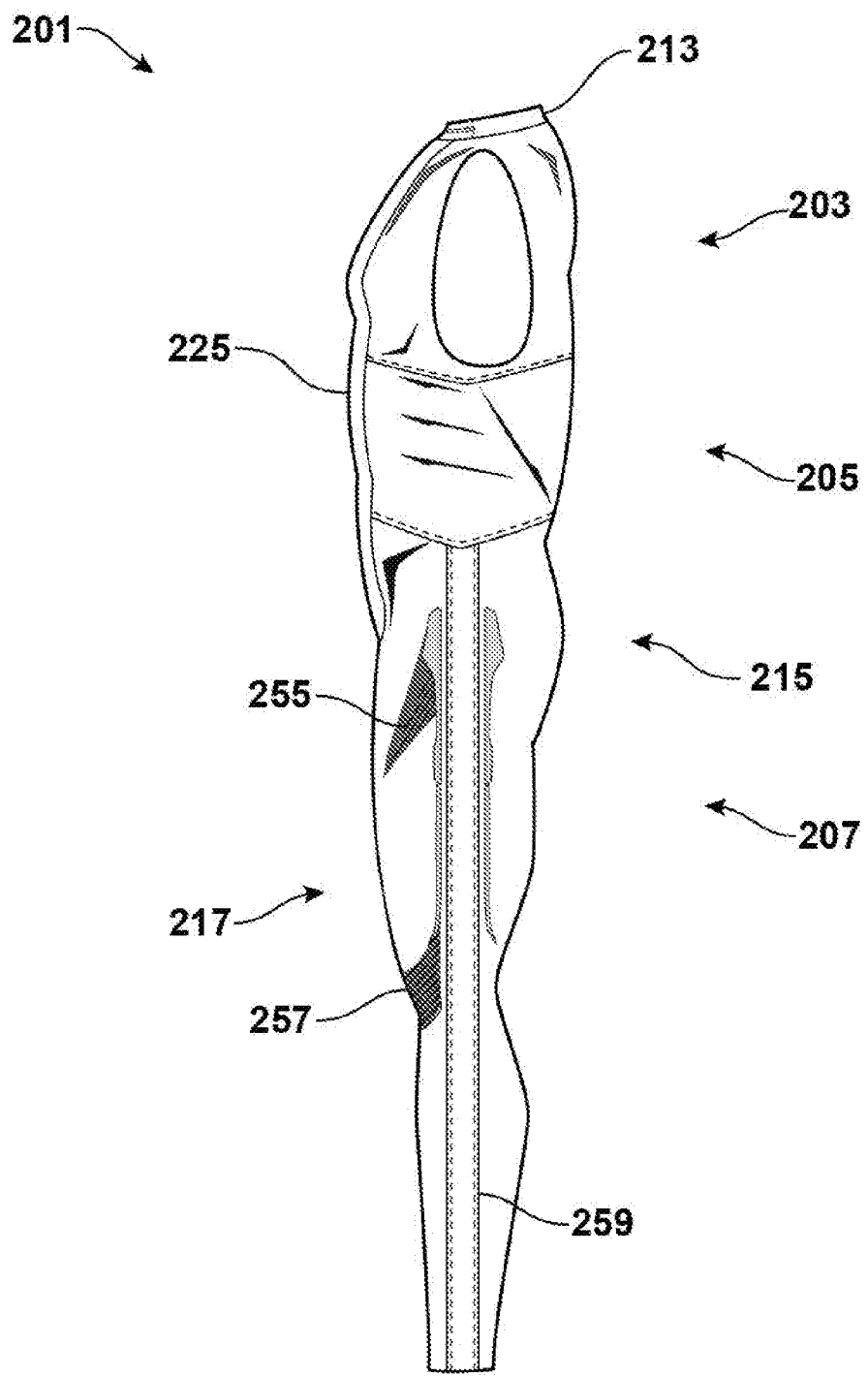
FIG. 8 is a side view (left side) of the wetsuit of FIG. 5; the left arm has been removed for clarity of illustration.
Figure 9:
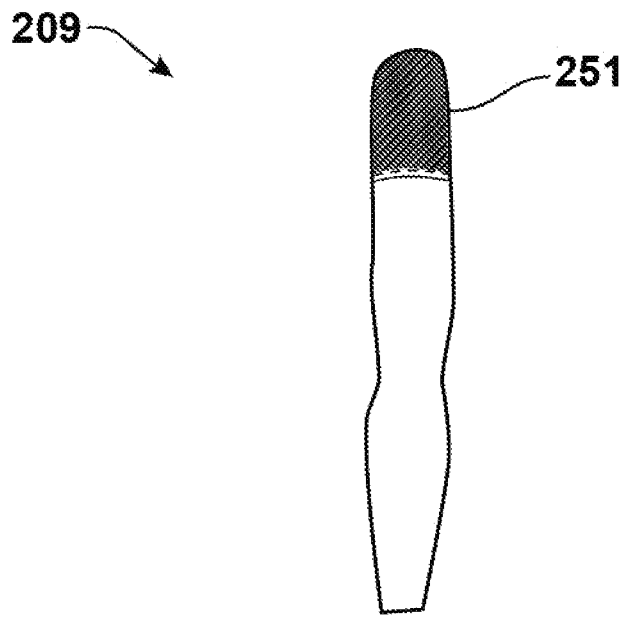
FIG. 9 is a side view of the left arm of the wetsuit of FIG. 5.
Figure 10:
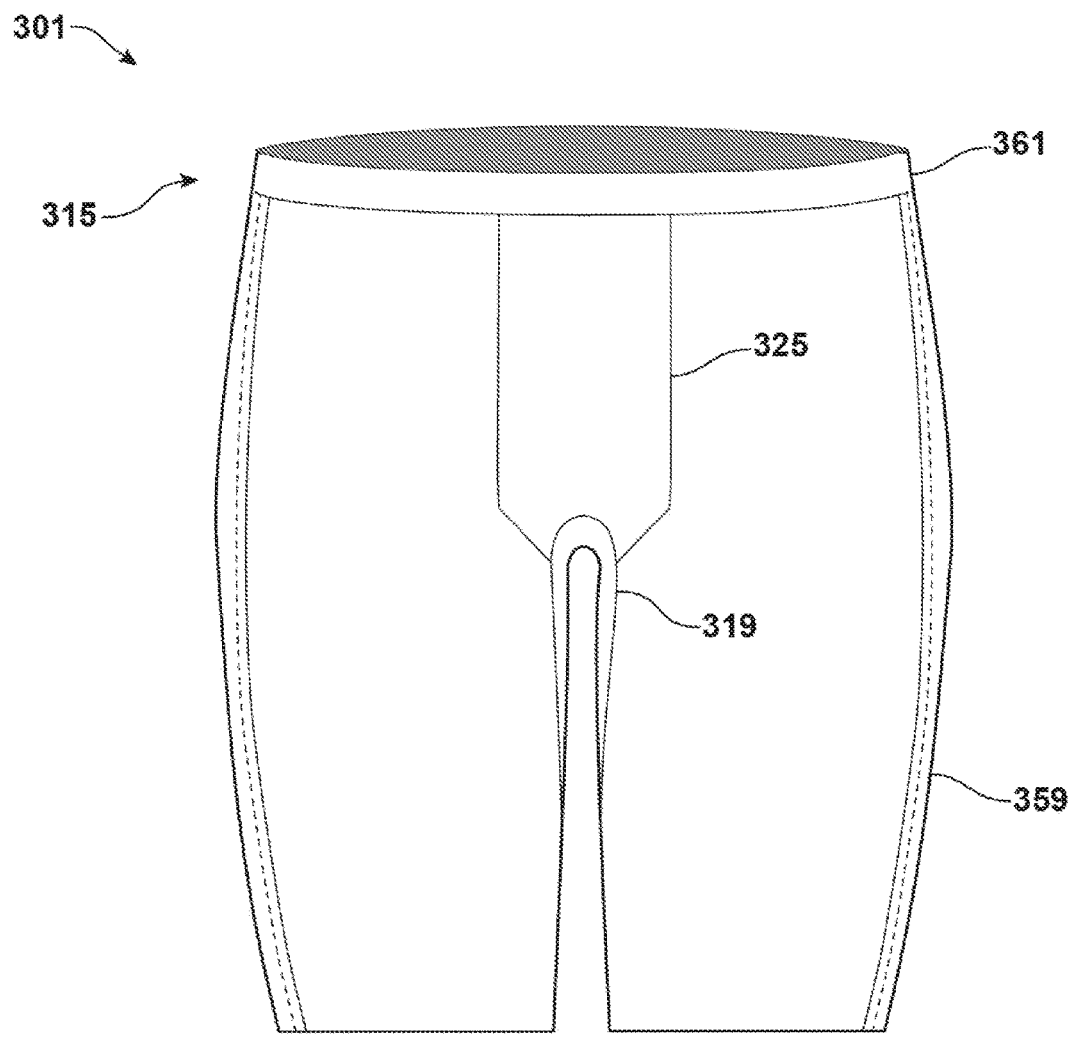
FIG. 10 is a front view of a third embodiment of a wetsuit in accordance with the teachings herein.
Figure 11:
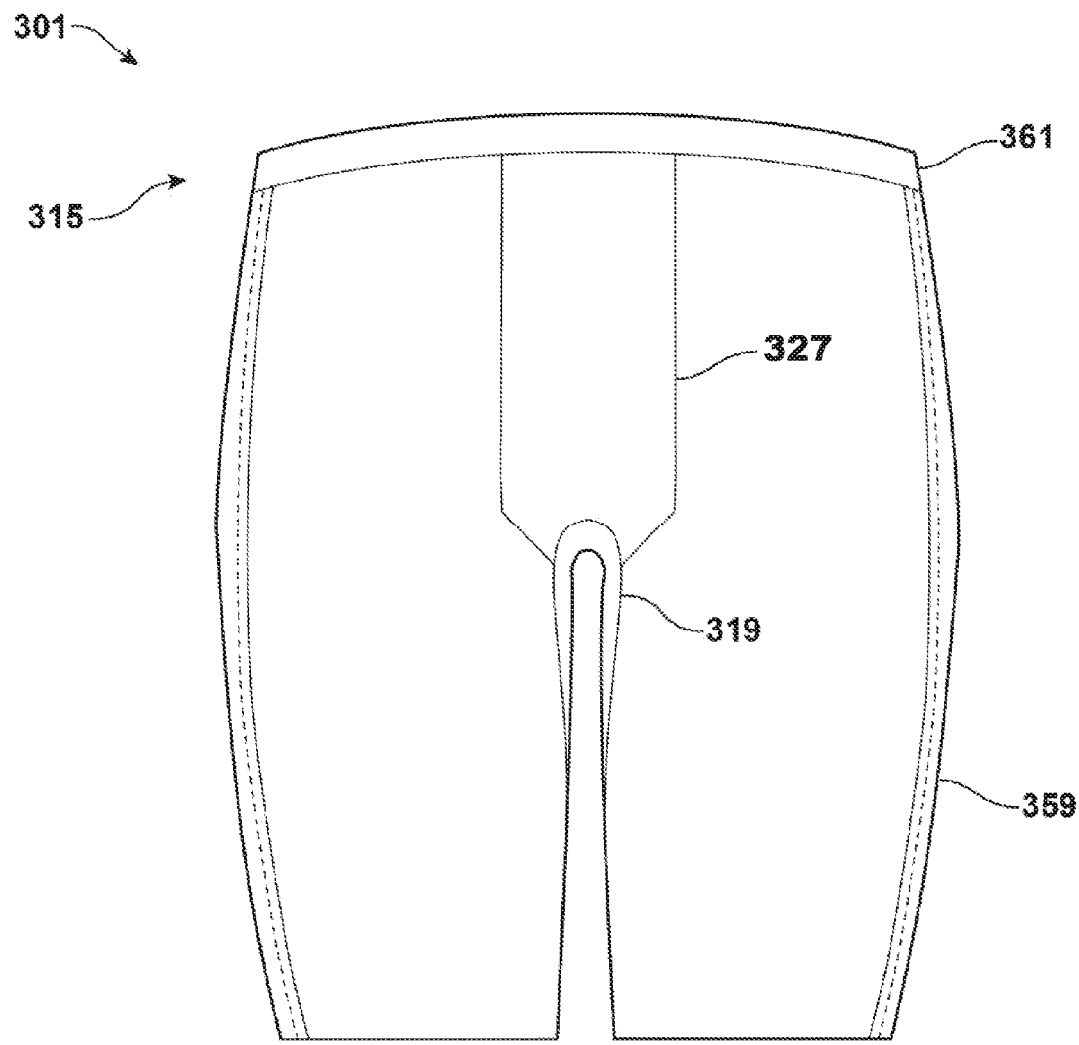
FIG. 11 is a rear view of the wetsuit of FIG. 10.
Figure 12:
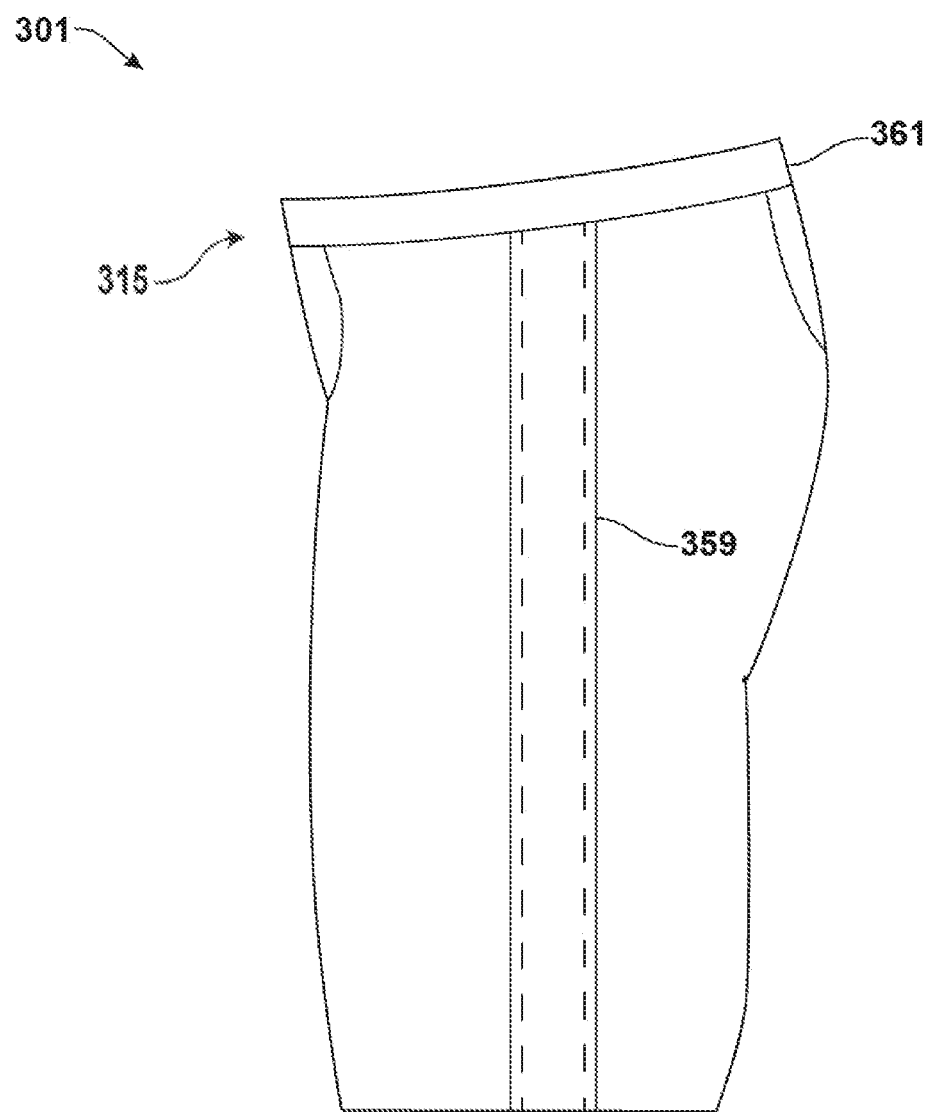
FIG. 12 is a side view (left side) of the wetsuit of FIG. 10.
Figure 13:
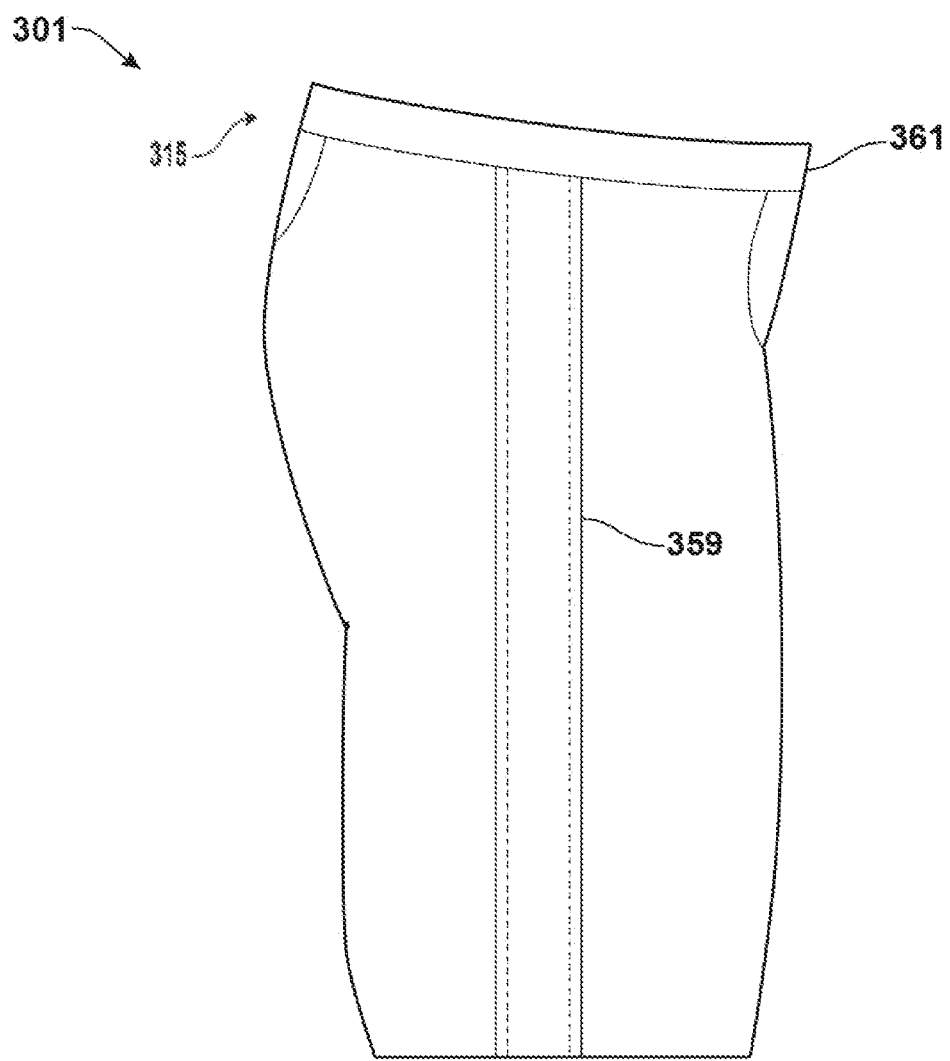
FIG. 13 is a side view (right side) of the wetsuit of FIG. 10.
Figure 14:
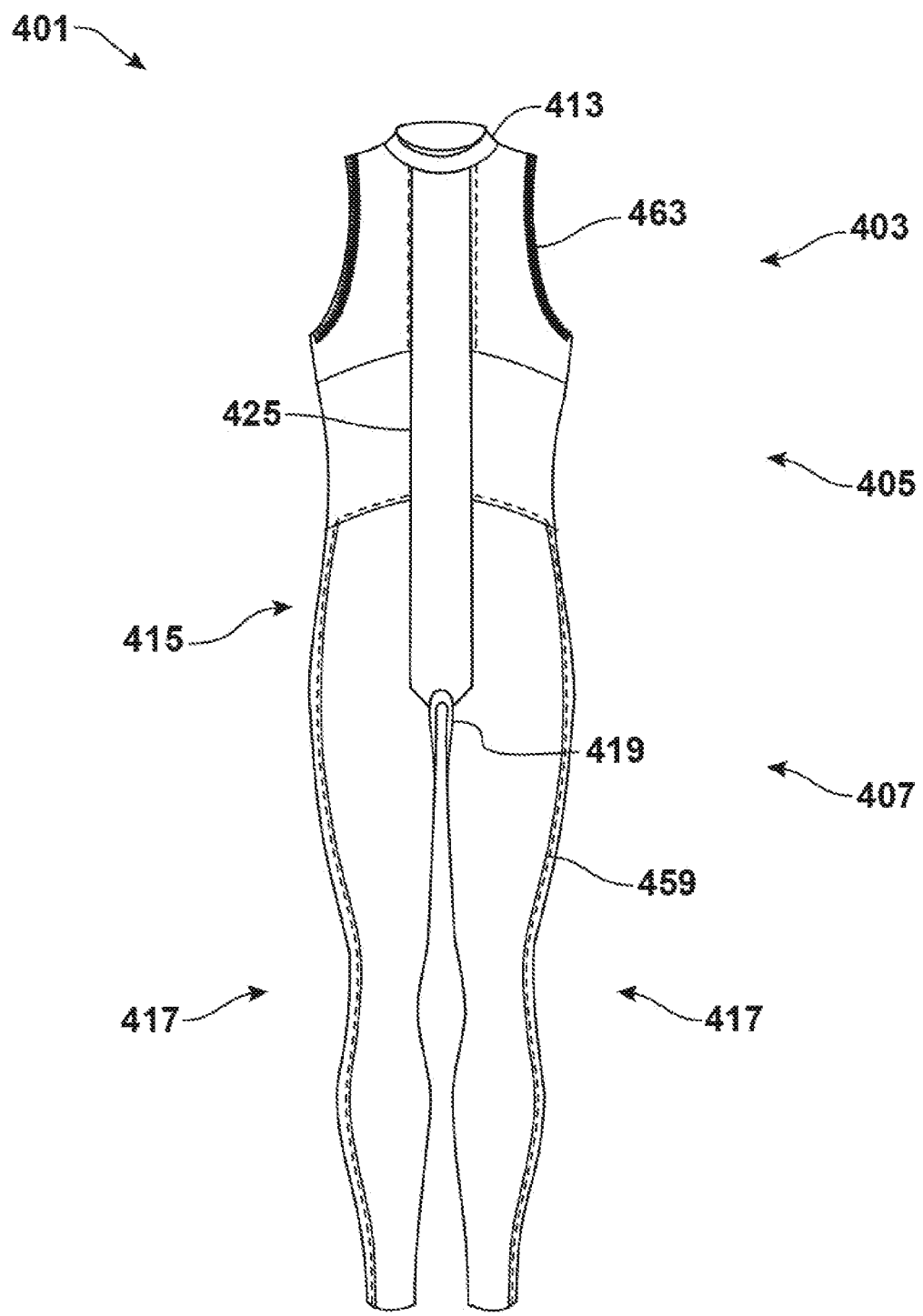
FIG. 14 is a front view of a fourth embodiment of a wetsuit in accordance with the teachings herein.

As seen in FIG. 6, the wetsuit 201 is equipped with a zipper 221 that extends down the back of the wetsuit 201 from the collar 213 to the bottom portion 207. A strap 223 is provided which allows the wearer to zip and unzip the wetsuit without help.

A first buoyancy enhancer 225 (see FIG. 5) is provided on the front of the wetsuit 201 in the form of a strip which extends from the collar 213 to the crotch 219. Similarly, a second buoyancy enhancer 227 (see FIG. 6) is provided on the back of the wetsuit 201 in the form of a strip which extends from the intersection between the top 203 and middle 205 portions to the crotch 219. The buoyancy enhancers 225, 227 in this embodiment function in a manner similar to the buoyancy enhancers 125, 127 of the embodiment of FIGS. 1-4.

While the wetsuit 201 of FIGS. 5-9 is similar in many respects to the wetsuit 101 of FIGS. 1-4 (ornamental aspects aside), the wetsuit 201 of FIGS. 5-9 has some additional features. In particular, the wetsuit 201 of FIGS. 5-9 is equipped with regions 251, 255 and 257 in which the material of the wetsuit 201 has greater flexibility to allow for freer movement in these areas. This may be accomplished, for example, by inserting panels of a thinner, more flexibly material into these areas. The thinner material may be, for example, a foamed polymeric material. Preferably, the bulk of the wetsuit comprises neoprene having a first thickness, regions 251, 255 and 257 comprise neoprene having a second thickness which is less than the first thickness, and the buoyancy enhancers 225, 227 comprise neoprene having a third thickness which is greater than the second thickness. Most preferably, the density of the material of the buoyancy enhancers 225, 227 is $d_1$, the density of the material from which the bulk of the wetsuit is made is $d_2$, and the density of the material of regions 251, 255 and 257 is $d_3$, and $d_1 < d_2 \leq d_3$.

The wetsuit 201 of FIGS. 5-9 is further equipped with drag strips 253 on the inner forearms of the wetsuit 201. These drag strips 253 are configured to increase the resistance of this portion of the wetsuit 201, thus improving the power and energy efficiency of the wearer's swimming stroke during the down stroke (e.g., in a traditional freestyle stroke). In a preferred embodiment, the drag strips comprise a plurality of ribs whose longitudinal axes are more or less perpendicular to the longitudinal axis of the wearer's forearm (and the longitudinal axis of the sleeve 209). These strips also provide improved proprioception or "feel for the water," which is important in swimming. This orientation allows the drag strips to "grip" the water, thus helping to propel the wearer through the water. In some embodiments, a portion of a suitable textile may be utilized in this part of the wetsuit to improve proprioception.

The wetsuit 201 of FIGS. 5-9 is further equipped with strips 259 on the sides of the leg portions 217. The strips 259 help to lessen resistance as the wearer moves through the water by covering the seam that exists between opposing edges of the fabric of the leg portions 217. In some embodiments, the strips 259 may also comprise a low density material to further improve the buoyancy of the wearer. Thus, for example, in some embodiments, the bulk of the leg portions may comprise a foamed polymeric material (such as, for example, neoprene) which has a thickness within the range of about 3 mm to about 6 mm, and more preferably a thickness within the range of about 4 mm to about 5 mm, while the strips 259 preferably have a thickness within the range of about 0.5 mm to about 2.5 mm, and more preferably have a thickness within the range of about 1 mm to about 2 mm. In some variations, the terminal portions of the leg portions that extend about the ankles of the wearer may also have a thickness within the range of about 0.5 mm to about 2.5 mm, and more preferably have a thickness within the range of about 1 mm to about 2 mm, to facilitate exit from the wetsuit. These terminal portions preferably have a length that is less than 2 inches, and more preferably have a length within the range of about 0.5 inches to about 1 inch.

FIGS. 10-13 depict a first particular, non-limiting embodiment of a swimsuit in accordance with the teachings herein. The swimsuit 301 depicted comprises a waist portion 315 that extends around the waist of the wearer, a waist strap 361 which secures the waist portion 315 to the body of the user (and which may include, for example, a suitable elastic material, a drawstring, or both, or any other suitable means to secure the waist portion 315 to the body of the user), and a crotch portion 319. A first buoyancy enhancer 325 is provided on the front of the swimsuit 301 in the form of a strip which extends from the waist strap 361 to the crotch portion 319. Similarly, a second buoyancy enhancer 327 (see FIG. 11) is provided on the back of the swimsuit 301 in the form of a strip which also extends from the waist strap 361 to the crotch portion 319. The buoyancy enhancers 325, 327 in this embodiment function in a manner similar to the buoyancy enhancers 125, 127 of the embodiment of FIGS. 1-4.

The swimsuit 301 of FIGS. 10-13 is further equipped with strips 359 on the sides of the waist portion 315. The strips 359 in this embodiment serve a similar function as the strips 259 in the embodiment of FIGS. 5-9.

FIGS. 14-17 depict a fourth particular, non-limiting embodiment of a wetsuit in accordance with the teachings herein. The wetsuit 401 depicted comprises a top portion 403, a middle portion 405 and a bottom portion 407. The top portion 403 extends around the shoulders and chest of the wearer. Unlike the embodiment of the wetsuit 101 of FIGS. 1-4, the wetsuit in this embodiment is sleeveless, and is instead equipped with openings 463 through which the wearer's arms protrude. The top portion 403 terminates at one end in a collar 413 which extends around the neck of the wearer, and terminates at the other end at the middle portion 405. The bottom portion 407 includes a waist portion 415 that extends around the waist of the wearer, leg portions 417 that extend down the legs of the wearer, and a crotch portion 419.

Figure 15:
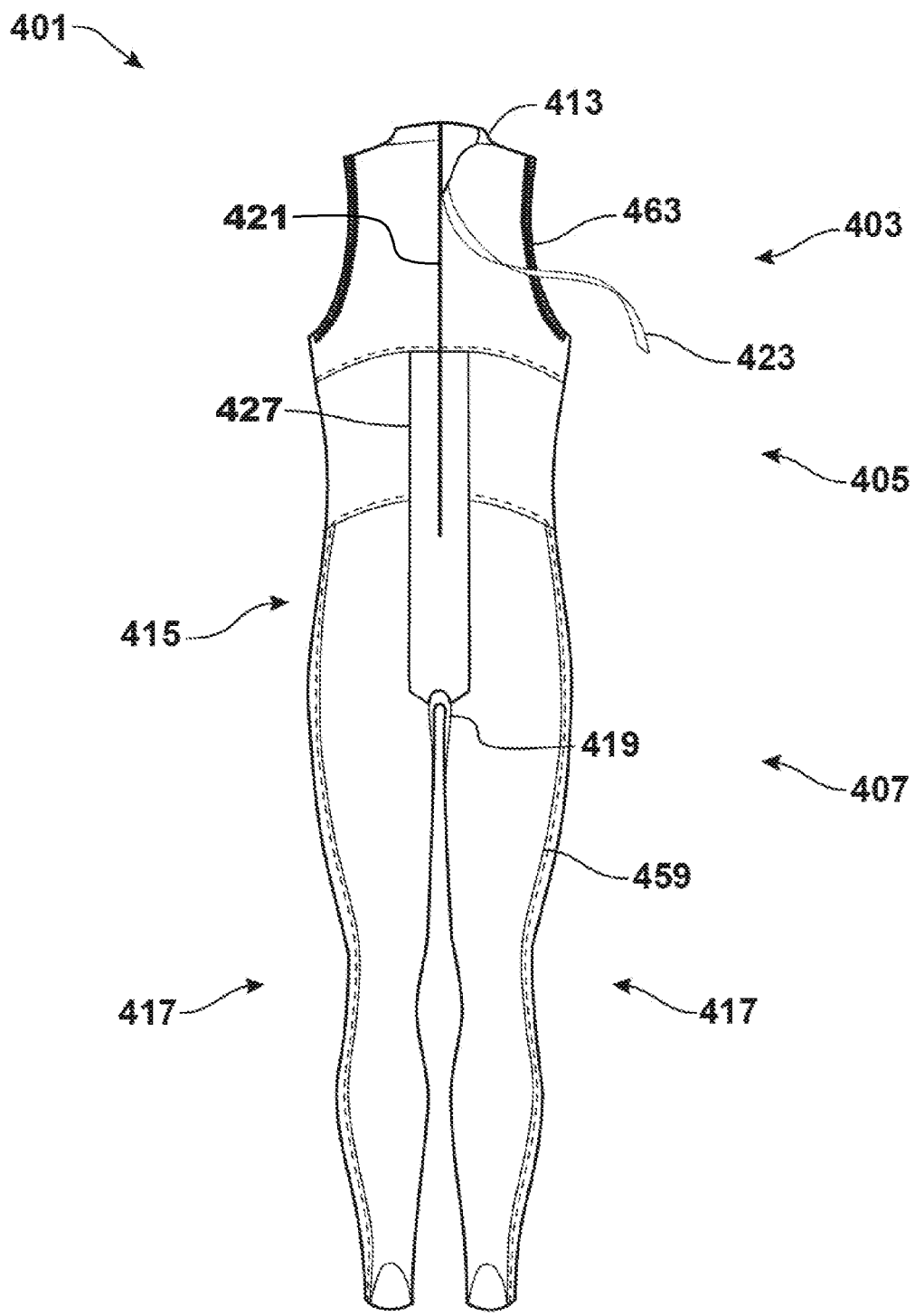
FIG. 15 is a rear view of the wetsuit of FIG. 14.
Figure 16:
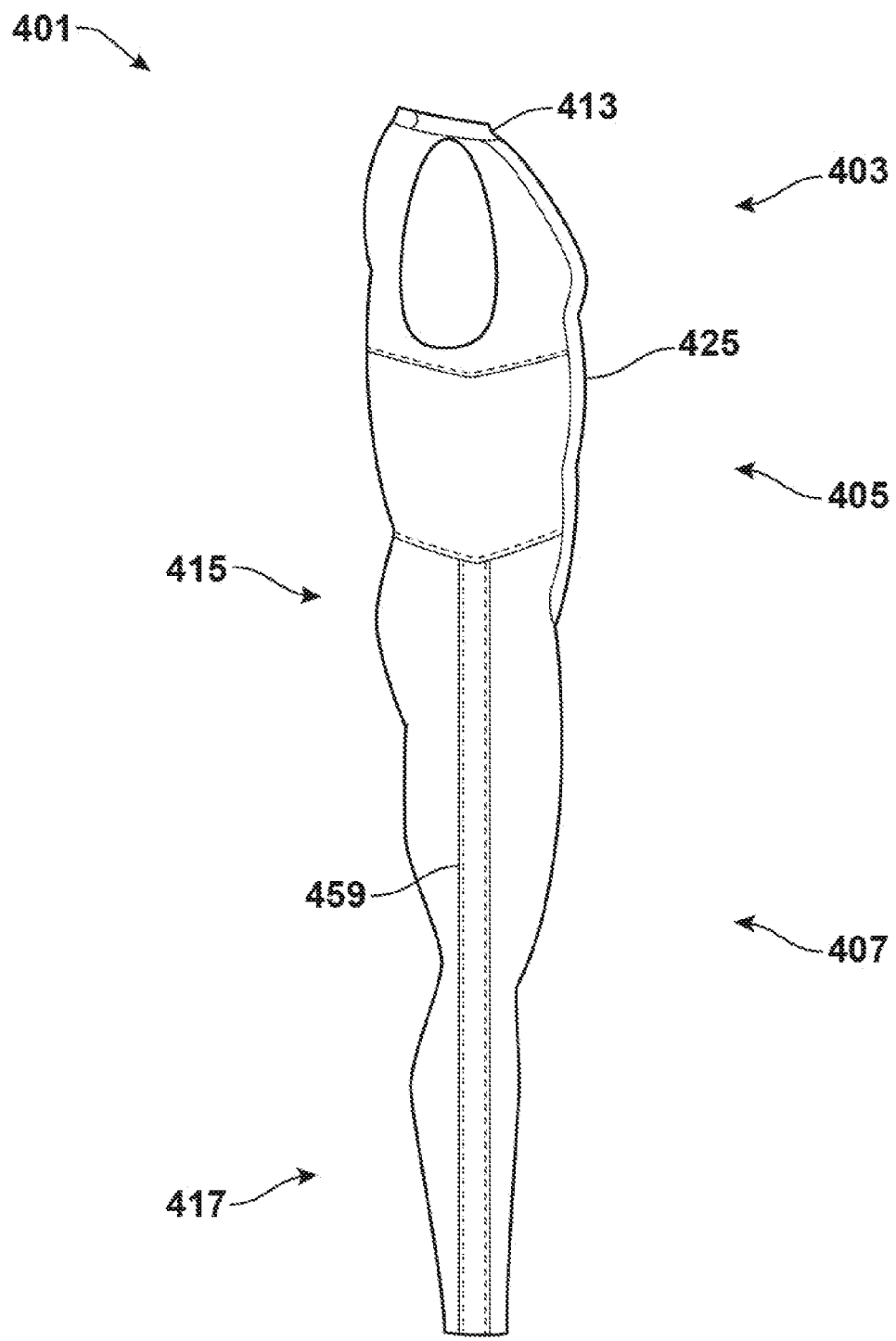
FIG. 16 is a side view (right side) of the wetsuit of FIG. 14; the right arm has been removed for clarity of illustration.
Figure 17:
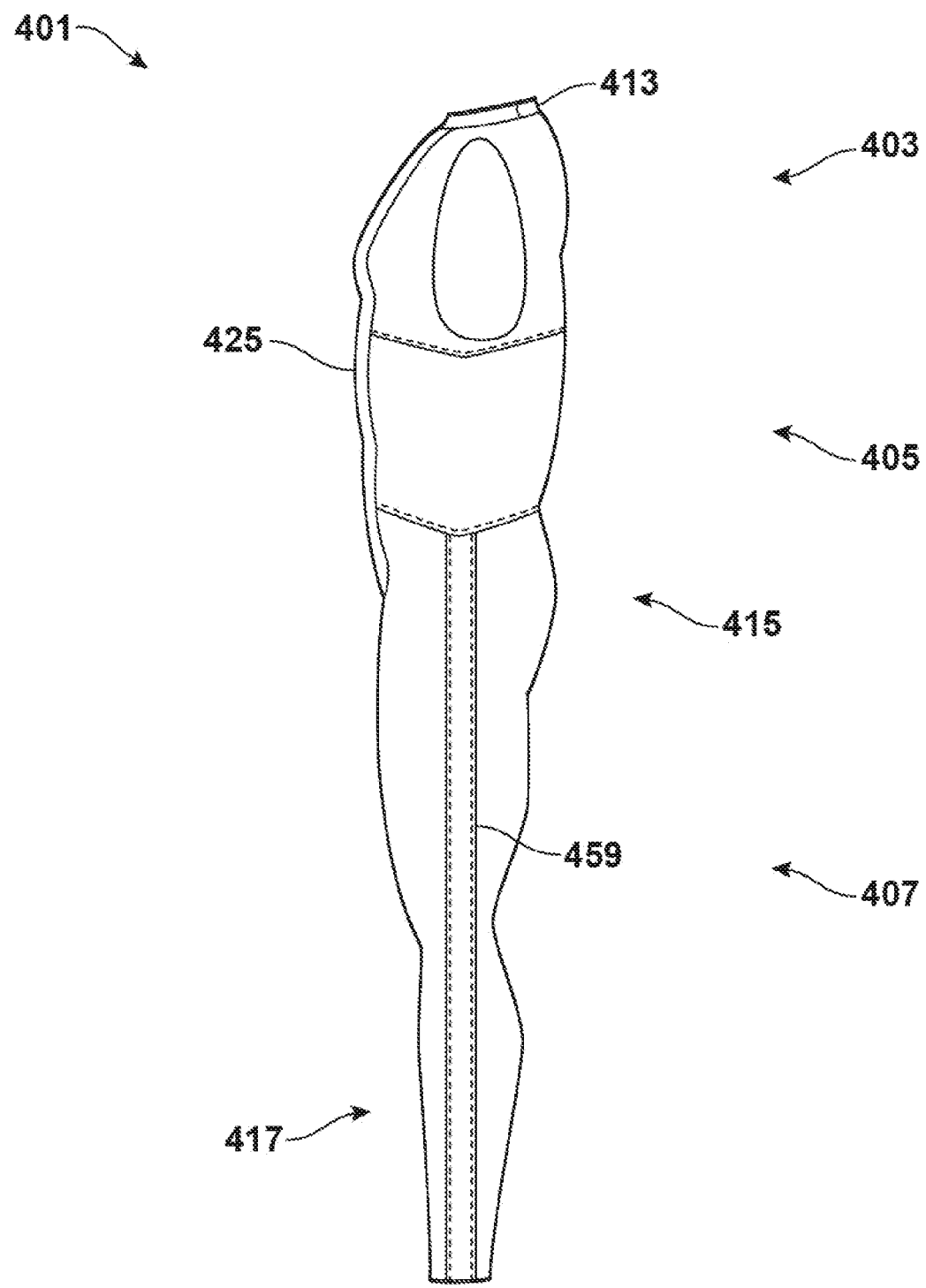
FIG. 17 is a side view (left side) of the wetsuit of FIG. 14; the left arm has been removed for clarity of illustration.

As seen in FIG. 15, the wetsuit 401 is equipped with a zipper 421 that extends down the back of the wetsuit 401 from the collar 413 to the bottom portion 407. A strap 423 is provided which allows the wearer to zip and unzip the wetsuit without help.

A first buoyancy enhancer 425 (see FIG. 14) is provided on the front of the wetsuit 401 in the form of a strip which extends from the collar 413 to the crotch 419. Similarly, a second buoyancy enhancer 427 (see FIG. 15) is provided on the back of the wetsuit 401 in the form of a strip which extends from the intersection between the top 403 and middle 405 portions to the crotch 419. The buoyancy enhancers 425, 427 in this embodiment function in a manner similar to the buoyancy enhancers 125, 127 of the embodiment of FIGS. 1-4.

The wetsuit 401 of FIGS. 14-17 is further equipped with strips 459 on the sides of the leg portions 417. The strips 459 help to reduce friction as the wearer moves through the water by covering the seam that exists between opposing edges of the fabric of the leg portions 417. In some embodiments, the strips 459 may also comprise a low density material to further improve the buoyancy of the wearer, which may also have the benefit of helping to achieve proper rotation of the wearer's body during swimming.

Figure 18:
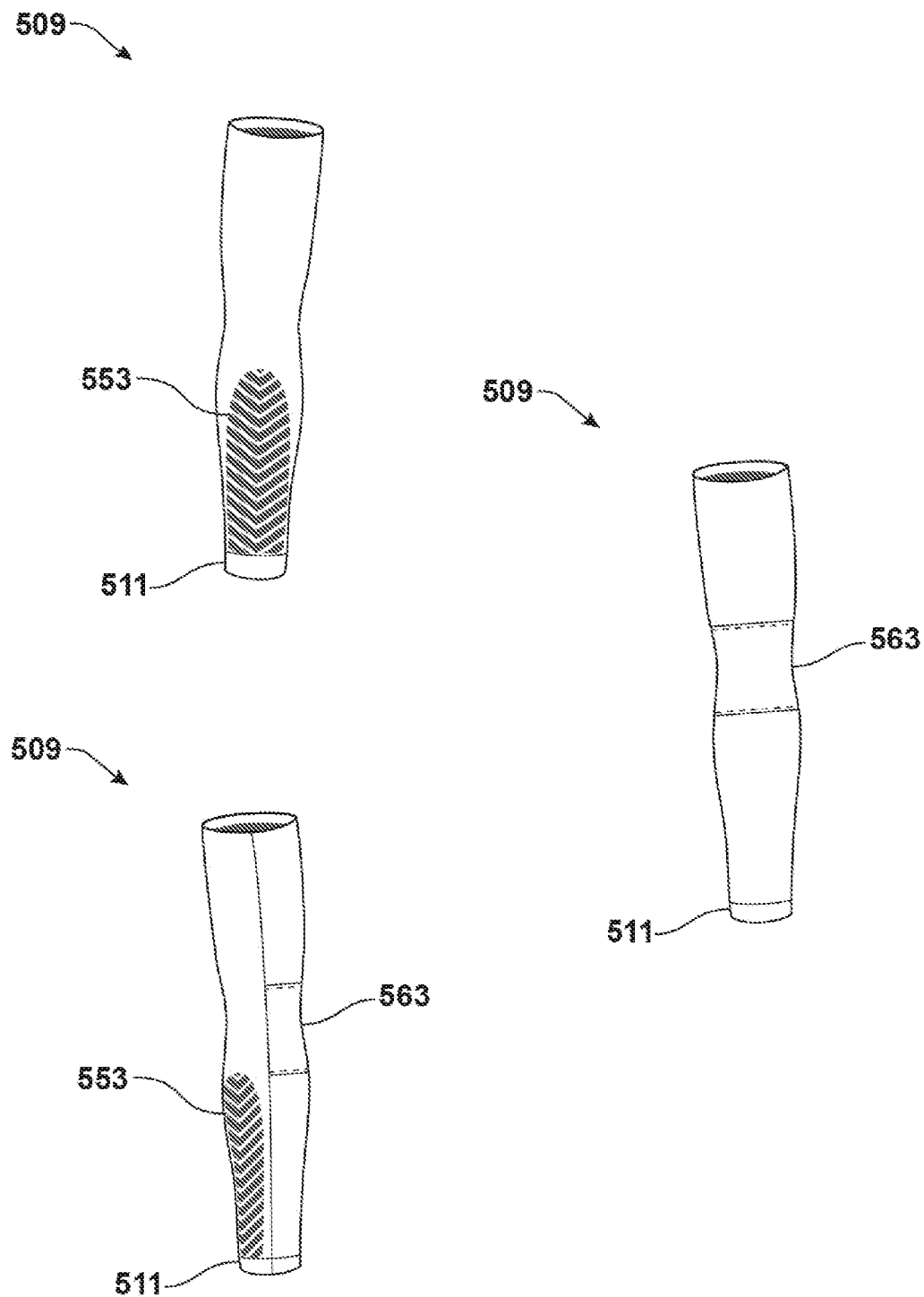
FIG. 18 is a series of illustrations showing (clockwise) the details of the front, back and side (right arm) of a first embodiment of a swimming sleeve.
Figure 19:
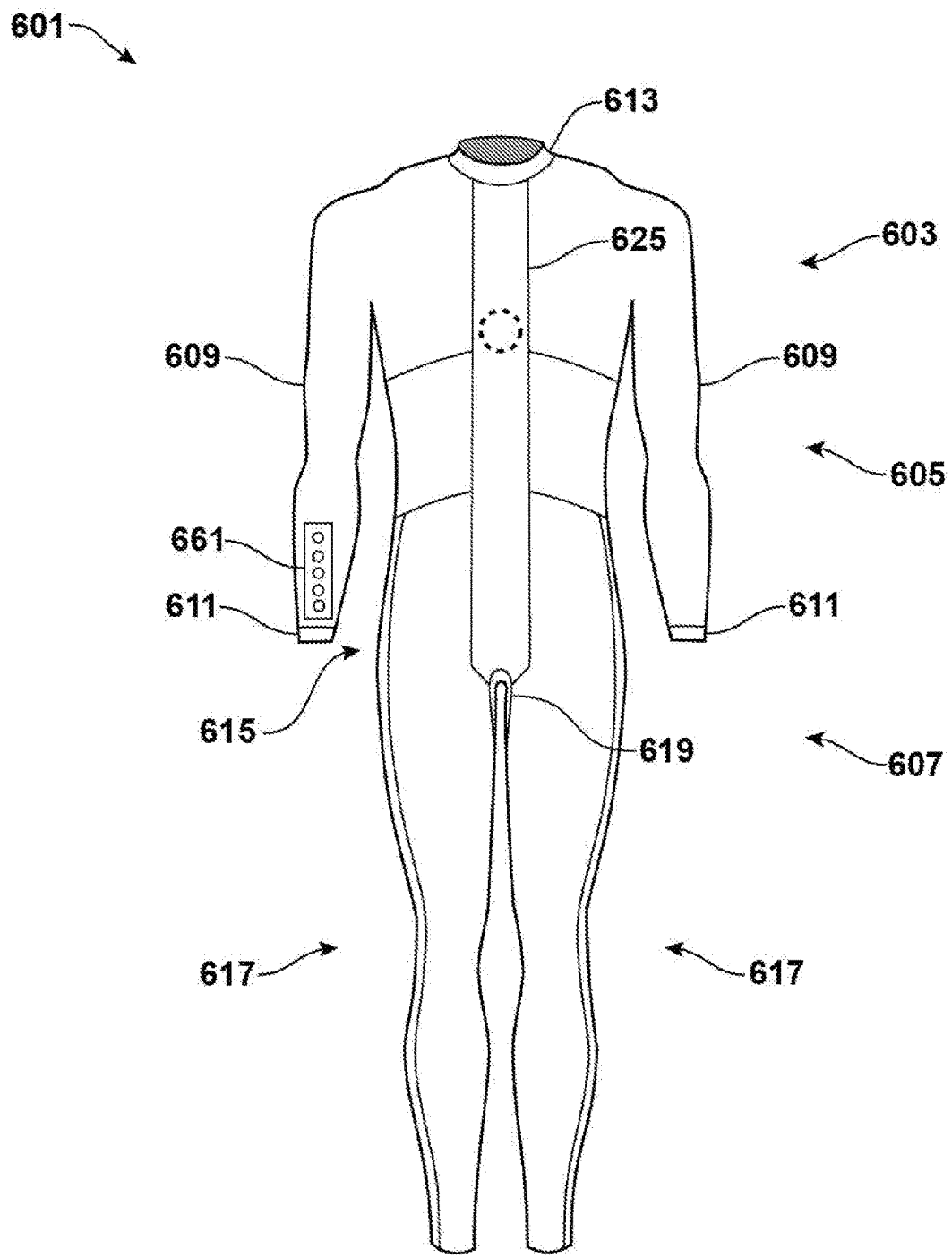
FIG. 19 is a front view of a fifth embodiment of a wetsuit in accordance with the teachings herein.

FIG. 18 depicts a particular, non-limiting embodiment of a swim sleeve in accordance with the teachings herein. The swim sleeve 509 depicted is a right-handed swim sleeve, and is shown (moving clockwise from top to bottom) from the front, back and right-hand side; for each figure, the corresponding left-handed version of the swim sleeve 509 is a mirror image.

The swim sleeve 509 terminates on one end in a cuff 511. The swim sleeve 509 is further equipped with drag strips 553, which serve a similar purpose to the drag strips 253 described with respect to the wet suit 201 of FIGS. 5-9. The swim sleeve 509 is also equipped with a region 563 in which the material of the swim sleeve 509 has greater flexibility to allow for freer movement in this area, similar to the regions 251, 255 and 257 in the wetsuit 201 of FIGS. 5-9.

The swim sleeve 509 may be used as a standalone device to enhance the swimming speed of the wearer. Alternatively, the swim sleeve 509 may be used in conjunction with a sleeveless wetsuit such as the wetsuit 401 of FIGS. 14-17 or the swimsuit 301 of FIGS. 10-13, in which case the resulting combination provides the user with the benefits of a sleeve, while also providing somewhat freer movement of the shoulders.

In still other embodiments, the swim sleeve 509 may be releasably attachable to a short sleeve wetsuit to provide the user with the option of swimming with a full or short sleeve wetsuit. In these embodiments, the swim sleeve 509 and/or the wetsuit may be equipped with suitable means for releasably attaching the swim sleeve 509 to the wetsuit.

FIGS. 19-22 depict a particular, non-limiting embodiment of a wetsuit in accordance with the teachings herein which is equipped with an electronics package. The wetsuit 601 depicted therein comprises a top portion 603, a middle portion 605 and a bottom portion 607. The top portion 603 extends around the shoulders and chest of the wearer, and includes sleeve portions 609 that extend down the arms of the wearer. Each of the sleeve portions 609 terminates in a cuff 611. The top portion 603 terminates at one end in a collar 613 which extends around the neck of the wearer, and terminates at the other end at the middle portion 605.

The bottom portion 607 includes a waist portion 615 that extends around the waist of the wearer, leg portions 617 that extend down the legs of the wearer, and a crotch portion 619.

Figure 20:
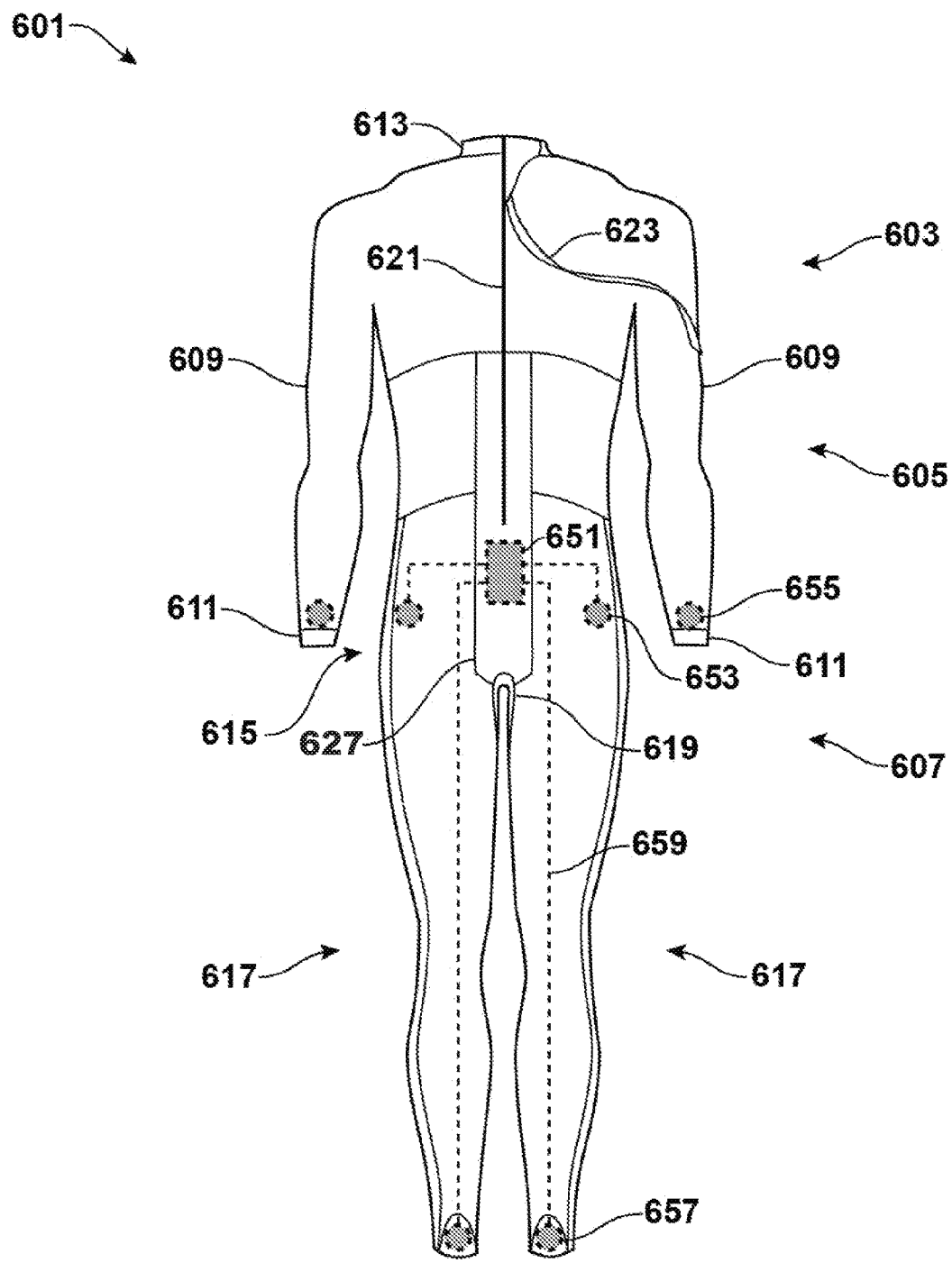
FIG. 20 is a rear view of the wetsuit of FIG. 19.
Figure 21:
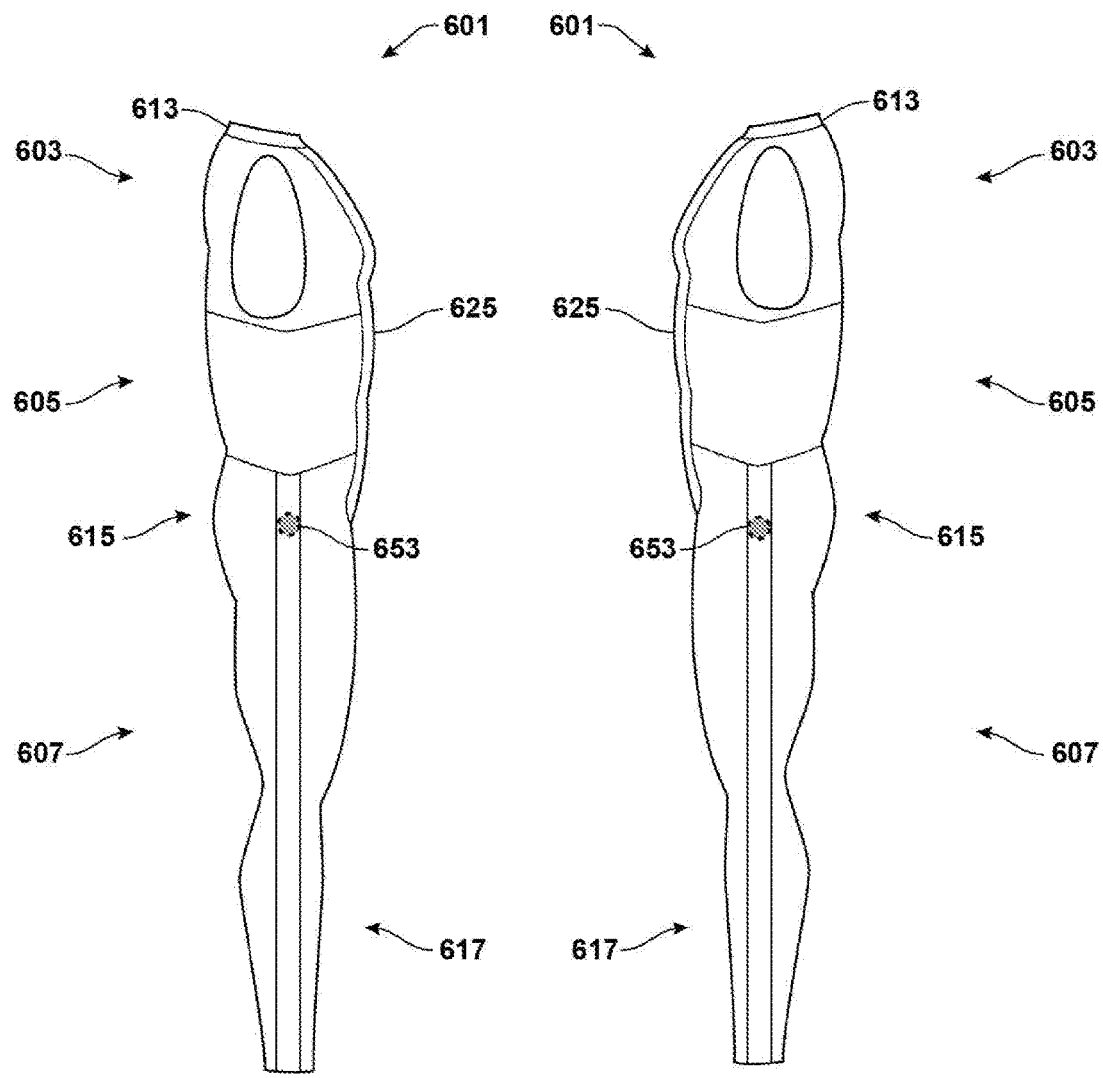
FIG. 21 is a side view (left and right sides) of the wetsuit of FIG. 19; the arms have been removed for clarity of illustration.

As seen in FIG. 20, the wetsuit 601 is equipped with a zipper 621 that extends down the back of the wetsuit 601 from the collar 613 to the bottom portion 607. A strap 623 is provided which allows the wearer to zip and unzip the wetsuit without help.

A first buoyancy enhancer 625 (see FIG. 19) is provided on the front of the wetsuit 601 in the form of a strip which extends from the collar 613 to the crotch 619. Similarly, a second buoyancy enhancer 627 (see FIG. 20) is provided on the back of the wetsuit 601 in the form of a strip which extends from the intersection between the top 603 and middle 605 portions to the crotch 619. The buoyancy enhancers 625, 627 in this embodiment function in a manner similar to the buoyancy enhancers 125, 127 of the embodiment of FIGS. 1-4.

The wetsuit 601 depicted is further equipped with a central processing unit (CPU) 651 or other suitable controller which, in the particular embodiment depicted, is in communication with first 653, second 655 and third 657 sets of accelerometers or other suitable sensors by way of suitable wires 659. The members of the first set 653 of accelerometers are preferably disposed in the waist portion 615 of the swimsuit 601 such that they lie over the hips of the wearer. The members of the second set 655 of accelerometers are preferably disposed in the arms 609 of the wetsuit 601 and preferably adjacent to the cuffs 611. The members of the third set 657 of accelerometers are preferably disposed in the leg portions 617 of the wetsuit 601, and preferably such that they are disposed near the feet of the wearer.

One or more displays 661 may be provided in one or both arms 609 of the wetsuit 601 (and are preferably disposed over the wrist of the wearer) which are in communication with the CPU 651 and/or the accelerometers 653, 655, 657 and which allow the wearer of the wetsuit 601 to view data or control the wetsuit features.

In use, the first set 653 of accelerometers may be utilized to collect information, for example, about the distance the wearer has traveled and the degree and rate of rotation of the wearer's hips (preferably as a function of time). The second 655 and third 657 sets of accelerometers may be utilized to collect information, for example, about the wearer's swimming cadence and the energy expended by the user (preferably over a period of time, or as a function of time).

The wetsuit 601 of FIGS. 19-22 offers a number of potential advantages, and may be utilized for various purposes. For example, in order to have success in competitive endurance events such as triathlons, a competitor must develop proper swimming mechanics, including a cadence that strikes a proper balance between maximizing speed and minimizing energy expenditure. The motion of a swimmer's hips, arms and legs, and the force with which those motions occur, are all important aspects of such mechanics. The wetsuit 601 of FIGS. 19-22 may be utilized to collect information about these mechanics, thus helping the wearer to identify flaws in their swimming mechanics, or to detect deviations from proper swimming mechanics which may occur over time (e.g., as the wearer becomes fatigued).

In some embodiments, the wetsuit may be equipped with appropriate means to generate visual or audio indicia or cues whenever deviations from proper swimming mechanics occur, thus helping the wearer to develop improved mechanics, avoid deviations from improper mechanics, and develop a better feel for when deviations from proper mechanics occur. Consequently, the wetsuit 601 of FIGS. 19-22 is useful not only as a competitive wetsuit (where permitted by applicable rules), but is also useful as a training device.

Several variations or modifications are possible to the wetsuit 601 of FIGS. 19-22. For example, the wetsuit depicted therein may be equipped with a GPS, which may be separate from, or integral with, the CPU or other control unit. The GPS, or one or more antennas associated therewith, are preferably disposed on the back of the wetsuit or in an associated swim cap. The GPS may be utilized for various purposes, including tracking the position of the wearer for data collection purposes or to inform the wearer when they are deviating from a desired course. Thus, for example, the GPS functionality may be utilized by open water swimmers to stay on course, despite distractions, currents, or other influences that may lead to course deviations.

The wetsuit 601 of FIGS. 19-22 may also be equipped with various other accessories. For example, the wetsuit may be equipped with goggles that interface with the CPU or GPS to offer heads-up display of performance or positional data. The wetsuit may also be equipped with a heart rate monitor, or may be adapted to interface with a heart rate monitor worn by the user. Such a heart rate monitor may, for example, be a strap-on unit that is affixed to the chest of the user with one or more straps, or may be a type that is affixed to the user's chest with a removable adhesive. The wetsuit may also be equipped with suitable transceivers to transmit, for example, data collected from sensors disposed in the wetsuit, or to receive data from an external source. The wetsuit may also be equipped with onboard memory (in the form of memory cards or other suitable media) to store data when necessary or desirable.

Moreover, while the wetsuit 601 of FIGS. 19-22 is depicted as having three sets of accelerometers, each of which has two members, one skilled in the art will appreciate that various other types of sensors may be utilized in place of, or in addition to, accelerometers. Moreover, any suitable number of accelerometers or other sensors may be utilized in wetsuits made in accordance with the teachings herein, and the placement of these accelerometers or other sensors may vary.

Furthermore, while the wetsuit 601 of FIGS. 19-22 has been described with reference to the use of wires to provide a communications conduit between the sensors and the CPU or GPS, it will be appreciated that various types of cables, optical fibers, wireless signals, or other suitable communications means may be utilized for communicating between such elements in wetsuits made in accordance with the teachings herein.

It will also be appreciated that the features described with respect to the wetsuit 601 of FIGS. 19-22 may be incorporated into the other wetsuits and swimsuits disclosed herein, with modifications where appropriate. For example, in sleeveless wetsuit embodiments, any electronics normally disposed in the sleeve portions may be moved to other portions of the wetsuit, or may be disposed in a separate swimming sleeve (or sleeves) and may communicate wirelessly with the components in the wetsuit.

It will also be appreciate that materials of various thicknesses, densities and dimensions may be employed in the wetsuits and swimsuits described herein. For example, the first buoyancy enhancers (e.g., elements 125 and 325 of FIGS. 1 and 10, respectively) in the wetsuits and swimsuits described herein preferably have widths within the range of about 1 inches to about 7 inches, and more preferably have widths within the range of about 4 inches to about 6 inches. The second buoyancy enhancers (e.g., elements 127 and 327 of FIGS. 2 and 11, respectively) in the wetsuits and swimsuits described herein preferably have the same or similar widths as the first buoyancy enhancers; however, while the first buoyancy enhancers preferably comprise an aerated polymeric material, the second buoyancy enhancers preferably do not comprise an aerated polymeric material, since non-aerated polymeric materials are typically more flexible and conform better to the lower back of the wearer.

The cuffs (e.g., element 111 in FIG. 1) have a width that is preferably in the range of about 1 to about 2 inches. In the swimming sleeves of FIG. 18, the cuffs 511 have a width that is preferably in the range of about 1 to about 3 inches. The strips (e.g., elements 259, 359 and 459 of FIGS. 8, 10 and 16, respectively) have a width that is preferably in the range of about 1 to about 3 inches. The waist strap (e.g., element 361 in FIG. 10) has a width that is preferably in the range of about 1 to about 2 inches. Region 563 in the swim sleeve 509 of FIG. 18 has a width that is preferably in the range of about 4 to about 6 inches. The drag strips 553 in the swim sleeve 509 of FIG. 18 occupy a region having a maximum width which is preferably within the range of about 6 to about 8 inches.

The swimwear described herein may also be equipped with, or used in conjunction with, a heart rate monitor. Preferably, the heart rate monitor is a manufactured plastic module (heart rate module, ANT+ and Bluetooth™ compatible, battery powered with removable battery and screw off door) coupled with an adhesive strip that affixes to the chest or another area where heart rate may be accurately measured. The use of an adhesive strip avoids the need for fabric straps, which can be uncomfortable. In some embodiments, the device may have a molded plastic female adapter that allows the heart rate module to be removably attached (e.g., by clipping it into place). This approach is similar to the adhesive strips for an infusion site for a type one diabetic, and such devices are produced, for example, by Medtronic Inc. (Minneapolis, Minn.). Such adhesive strips may be marketed as boxes of single use strips, and may be packaged with alcohol wipes to remove any extra adhesive. A heart rate monitor of this type may then be paired with a computer or watch for use during the cycling and running portions of a triathlon, without concern for movement or shifting during exercise.

The swimwear described herein may also be equipped with, or used in conjunction with, various heads up displays, which may be incorporated, for example, into a pair of swimming goggles. In some embodiments, such heads-up displays may utilize fiber optics or LEDs, either as a laminate on some part of the glass or as a separate module that is permanently or semi-permanently attached thereto. Such embodiments may be equipped with an operating system that receives information (e.g., performance data) from a CPU and generates light, vibration, or audio cues (or some combination of the foregoing) to apprise the user of the status or characteristics of the performance data. The heads-up display may include manual, automatic or voice activated controls to allow the user to cycle through display fields or types, to navigate a graphical user interface (GUI), and to perform other such functions. Preferably, the foregoing system is waterproof, shockproof, oil and sweat resistant, and generally very light and durable. In some embodiments, the swimwear described herein may also be equipped with, or used in conjunction with, a means for releasing odors that may trigger a known and desired physiological response.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A swimsuit comprising:
   a first central buoyancy enhancing region comprising an aerated polymeric material provided along a vertical centerline on a front of the swimsuit having a first buoyancy per unit area; and
   a lateral region disposed on either side of the first central buoyancy enhancing region having a second buoyancy per unit area that is greater than the first buoyancy per unit area of the first central buoyancy enhancing region;
   the swimsuit including a waist portion, a crotch portion, a first leg portion and a second leg portion, each leg portion configured to extend from the waist portion to at least the user's thigh region, and
   the first central buoyancy enhancing region extending from about the waist portion to the crotch portion.

2. The swimsuit of claim 1, wherein the first buoyancy per unit area of the first central buoyancy enhancing region is greater than the second buoyancy per unit area of the lateral region.

3. The swimsuit of claim 1, wherein the lateral region comprises a second material.

4. The swimsuit of claim 3, wherein the aerated polymeric material and the second material are the same.

5. The swimsuit of claim 3, wherein the second material comprises a non-aerated polymeric material.

6. The swimsuit of claim 1, wherein the first central buoyancy enhancing region comprises a first thickness and the lateral region comprises a second thickness.

7. The swimsuit of claim 6, wherein the first thickness and the second thickness are the same.

8. The swimsuit of claim 6, wherein the first thickness is greater than the second thickness.

9. The swimsuit of claim 1, wherein the first central buoyancy enhancing region has a width from about 1.0 in. (2.54 cm) to about 7.0 in (17.78 cm).

10. The swimsuit of claim 3, wherein the aerated polymeric material has a first density $\rho_1$ and the second material has a second density $\rho_2$.

11. The swimsuit of claim 3, further comprising a first lateral strip extending down a first lateral side of the first leg portion, wherein a lateral strip buoyancy per unit area of the first lateral strip is less than the buoyancy per unit area of the lateral region.

12. The swimsuit of claim 11, wherein the first lateral strip comprises a third material.

13. The swimsuit of claim 11, wherein the first lateral strip comprises a third thickness.

14. The swimsuit of claim 13, wherein a second thickness of the second material in the lateral region is greater than the third thickness.

15. The swimsuit of claim 3, wherein the aerated polymeric material has a first thickness from about 0.118 in (3.0 mm) to about 0.197 in (5.0 mm).

16. The swimsuit of claim 3, wherein the second material has a second thickness from about 0.078 in (2.0 mm) to about 0.118 in (3.0 mm).

17. The swimsuit of claim 11, wherein the first lateral strip comprises a low density polymeric material or neoprene.

18. The swimsuit of claim 13, wherein the third thickness of the first lateral strip is from about 0.02 in (0.5 mm) to about 0.10 in (2.5 mm).

19. The swimsuit of claim 1, further comprising a second central buoyancy enhancing region provided along the vertical centerline on a back of the swimsuit extending from about the waist portion to the crotch portion.

20. The swimsuit of claim 19, wherein the second central buoyancy enhancing region comprises material that is the same material as the first central buoyancy enhancing region.

21. The swimsuit of claim 19, wherein the second central buoyancy enhancing region comprises a different material than the first central buoyancy enhancing region.

22. The swimsuit of claim 19, wherein the second central buoyancy enhancing region comprises a more flexible material than the first central buoyancy enhancing region.

23. The swimsuit of claim 19, wherein the second central buoyancy enhancing region comprises a non-aerated polymeric material.

24. The swimsuit of claim 19, wherein the second central buoyancy enhancing region comprises a fourth thickness that is different from the first central buoyancy enhancing region.

25. The swimsuit of claim 19, wherein the second central buoyancy enhancing region comprises a fourth thickness that is the same as the first central buoyancy enhancing region.

26. The swimsuit of claim 19, wherein the second central buoyancy enhancing region has a width from about 1.0 in. (2.54 cm) to about 7.0 in (17.78 cm).

27. The swimsuit of claim 19, wherein the second central buoyancy enhancing region has a density that is the same density as the first central buoyancy enhancing region.

28. The swimsuit of claim 19, further comprising:
a first lateral strip extending down a first lateral side of the first leg portion wherein a lateral strip buoyancy per unit area of the first lateral strip is less than a leg portion buoyancy per unit area of the first leg portion;
wherein the lateral region further comprises;
a first anterior lateral region between the first central buoyancy enhancing region and the first lateral strip, configured to extend over a first anterior hip region of a torso of the user;
a first posterior lateral region between the second central buoyancy enhancing region and the first lateral strip, configured to extend over a first posterior hip region of the torso of the user.

29. The swimsuit of claim 1, wherein the waist portion further comprises a waist strap with securing means configured to secure the waist portion of the swimsuit to the body of the user, the securing means comprising:
an elastic material;
a drawstring;
a zipper;
a hook and loop fastener; or
a releasable fastener.

30. The swimsuit of claim 11, wherein the first lateral strip comprises a different density than the first central buoyancy enhancing region.

\* \* \* \* \*